United States Patent [19]

Dininno et al.

[11] Patent Number: 5,004,740
[45] Date of Patent: Apr. 2, 1991

[54] 2-PHENANTHRENYL-CARBAPENEM ANTIBACTERIAL AGENTS

[75] Inventors: Frank P. Dininno, Old Bridge; Thomas N. Salzmann, North Plainfield; Mark L. Greenlee, Rahway, all of N.J.

[73] Assignee: Merck & Co., Inc., Rahway, N.J.

[21] Appl. No.: 543,990

[22] Filed: Jun. 26, 1990

[51] Int. Cl.$^5$ .................. C07D 487/04; A61K 31/40
[52] U.S. Cl. .................................. 514/210; 540/302
[58] Field of Search ...................... 540/302; 514/210

[56] References Cited

U.S. PATENT DOCUMENTS

| 4,260,627 | 4/1981 | Christensen et al. | 424/274 |
|---|---|---|---|
| 4,465,632 | 8/1984 | Christensen et al. | 260/245.2 |
| 4,543,257 | 9/1985 | Cama et al. | 514/210 |
| 4,775,669 | 10/1988 | Cama et al. | 514/210 |
| 4,962,101 | 10/1990 | Dininno | 514/210 |

FOREIGN PATENT DOCUMENTS 0277743 8/1988 European Pat. Off. .

OTHER PUBLICATIONS

L. D. Cama et al., Total Synthesis of Thienamycin Analogs-III, Tetrahedron 39, 2531 (1983).
R. N. Guthikonda, et al., Structure Activity Relationships in the 2-Arylcarbapenem Series, *J. Med. Chem.*, 30, 871 (1987).

*Primary Examiner*—Robert Gerstl
*Attorney, Agent, or Firm*—John W. Harbour; Hesna J. Pfeiffer

[57] ABSTRACT

Carbapenems of the formula

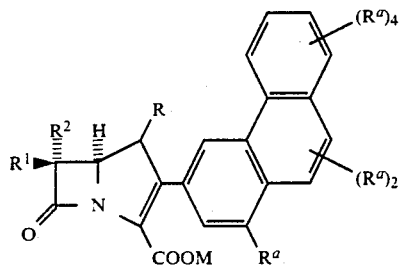

are useful antibacterial agents.

21 Claims, No Drawings

2-PHENANTHRENYL-CARBAPENEM ANTIBACTERIAL AGENTS

BACKGROUND OF THE INVENTION

The present invention relates to antibacterial agents of the carbapenem class, in which the 2-position sidechain is characterized by a phenanthrene moiety, substituted by various cationic and neutral substituents, as described in more detail further below.

Thienamycin was an early carbapenem antibacterial agent having a broad spectrum; it has the following formula:

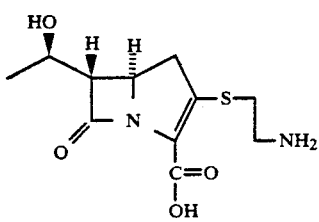

Later, N-formimidoyl thienamycin was discovered; it has the formula:

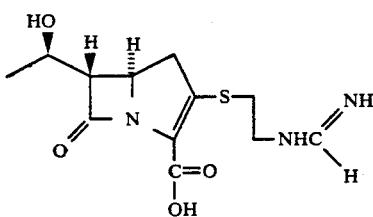

The 2-phenanthrenyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

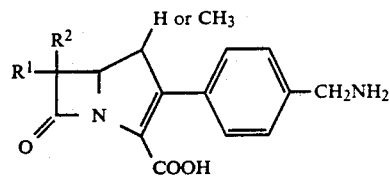

However, there is no description or suggestion of a phenanthrenyl 2-substituent such as characterizes the compounds of the present invention, nor is there any suggestion of the suprisingly better anti-MRSA/MRCNS activity of the compounds of the present invention.

EP-A-0277 743 describes a particular class of compounds of the formula:

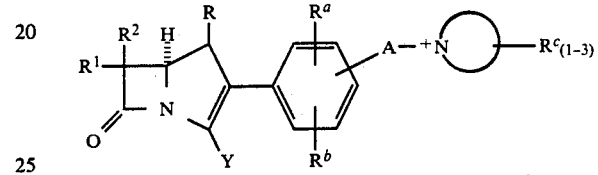

but this limited teaching in no way suggests the totally different compounds of the present invention, nor their surprisingly better anti-MRSA/MRCNS activity.

SUMMARY OF INVENTION

The present invention provides novel carbapenem compounds of the formula:

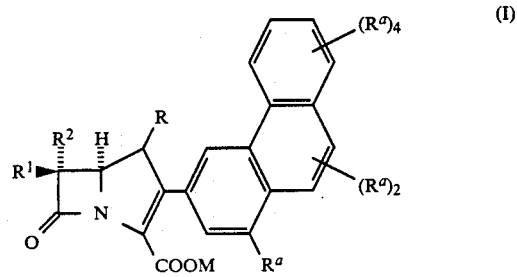

wherein:

R is H or $CH_3$;

$R^1$ and $R^2$ are independently H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$, or $(CH_3)_2C(F)-$;

$R^a$ are independently selected from the group consisting of hydrogen and the radicals set out below, provided that one but not more than one $R^a$ is selected from Type I substituents, the remaining non-hydrogen substituents being selected from Type II, and in total not more than four $R^a$ radicals are other than hydrogen:

I.

(a)

where

A is $(CH_2)_m$—Q—$(CH_2)_n$, where m is 0 to 6 and n is 1 to 6 and Q is a covalent bond, O, S, SO, $SO_2$, NH, —$SO_2NH$—, —$NHSO_2$—, —CONH—, —NHCO—, —$SO_2N(C_1$–$C_4$alkyl)—, —$N(C_1$–$C_4$alkyl)$SO_2$—, —$CON(C_1$–$C_4$alkyl)—, —$N(C_1$–$C_4$alkyl)CO—, —CH=CH—, —CO—, —OC(O)—, —C(O)O— or $N(C_1$–$C_4$alkyl) and $(CH_2)_m$ is attached to the phenanthrenyl moiety;

is a 5- or 6-membered noncyclic heterocycle or an 8-, 9- or 10-membered bicyclic heterocycle, the heterocycle containing a first nitrogen in an aromatic 5- or 6-membered first ring, with attachment of the heterocycle to A by way of said first nitrogen and said first nitrogen is quaternary by virtue of the attachment and ring bonds, with the first ring containing 0 or 1 of either O or S, with the first ring containing 0 to 3 additional nitrogen atoms, with the first ring optionally fused to a 3- or 4-membered moiety to form the optional second ring, with the the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is $R^a$ as defined under II below, hydrogen, or —$NR^yR^z$ (where $R^y$ and $R^z$ are defined in II below), but independently selected from $R^a$ and from each other if more than one $R^c$ is present, and is attached to a carbon ring atom or a nitrogen heteroatom the valency of which is not satisfied by the ring bonds;

(b)

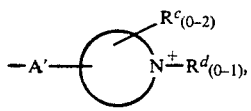

where

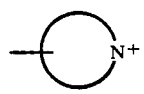

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen quaternary by virtue of a substituent $R^d$ in addition to the ring bonds thereto, with said first nitrogen neutral in the absence of a substituent $R^d$, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is defined above;

$R^d$ is hydrogen, $NH_2$, $O^-$ or $C_1$–$C_4$alkyl (where the alkyl group is optionally mono-substituted with $R^q$ as defined under IIc below);

A' is $(CH_2)_m$—Q—$(CH_2)_n$, where m is 0 to 6 and n is 0 to 6, Q is given above, and when m and n are 0 then Q is not a covalent bond;

(c) —$A_p$—$N^+R^y(R^w)0$–$1(R^z)$ where $R^y$ and $R^z$ are as defined under II below, $R^y$ and $R^z$ may further be together a $C_2$–$C_4$ alkylidene radical to form a ring (optionally mono-substituted with $R^q$ as defined below) interrupted by $N(O)R^e$ or $N^+(R^e)_2$ (where $R^e$ is hydrogen, $C_1$–$C_4$ alkyl, or $C_1$–$C_4$ alkyl mono-substituted with $R^q$ as defined below), $R^w$ is hydrogen, $C_{1-4}$ alkyl, $O^-$, $NH_2$, or absent in which case the $N^+$ is neutral, $R^w$, $R^y$ and $R^z$ may further together form a $C_5$–$C_{10}$ tertiary alkylidene radical which with $N^+$ forms a bicyclic ring, where the tertiary alkylidene radical is optionally mono-substituted with $R^q$ as defined below and where the tertiary carbon of the tertiary alkylidene radical is optionally replaced with nitrogen, $N^+R^e$ (where $R^e$ is defined above), or $N^+$—$O^-$, p is 0 or 1, and A is as defined above;

(d)

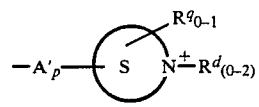

where

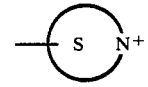

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen quaternary by virtue of one or two substituents $R^d$ in addition to the ring bonds thereto, with the first nitrogen alternatively neutral by virtue of zero or one substituents $R^d$ in addition to the ring bonds thereto with attachment of the heterocycle to A' by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), $S(O)_2$ and $NR^e$ where $R^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

$R^d$ is defined above and where more than one $R^d$ is present on a nitrogen, at least one $R^d$ is hydrogen or $C_1$-$C_4$ alkyl;

A' is defined above; and p is defined above;

$R^q$ is defined below;

II.
  (a) a trifluoromethyl group: —$CF_3$;
  (b) a halogen atom: —Br, —Cl, —F, or —I;
  (c) $C_1$-$C_4$ alkoxy radical: —$OC_{1-4}$ alkyl, wherein the alkyl is optionally mono-substituted by $R^q$, where
    $R^q$ is a member selected from the group consisting of —OH, —$OCH_3$, —CN, —$C(O)NH_2$, —$OC(O)NH_2$, CHO, —$OC(O)N(CH_3)_2$, —$SO_2NH_2$, —$SO_2N(CH_3)_2$, —$SOCH_3$, —$SO_2CH_3$, —F, —$CF_3$, —$COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);
  (d) a hydroxy group: —OH;
  (e) a carbonyloxy radical: —$O(C=O)R^s$, where
    $R^s$ is $C_{1-4}$ alkyl or phenyl, each of which is optionally mono-substituted by $R^q$ as defined above;
  (f) a carbamoyloxy radical: —$O(C=O)N(R^y)R^z$ where
    $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or —S(O)$_2$— to form a ring (where the ring is optionally mono-substituted with Rq as defined above);
  (g) a sulfur radical: —$S(O)_n$—$R^s$ where n=0-2, and $R^s$ is defined above;
  (h) a sulfamoyl group: —$SO_2N(R^y)R^z$ where $R^y$ and $R^z$ are defined above;
  (i) azido: $N_3$
  (j) a formamido group: —$N(R^t)(C=O)H$, where $R^t$ is is H or $C_{1-4}$ alkyl, and the alkyl thereof is optionally mono-substituted by $R^q$ as defined above;
  (k) a ($C_1$-$C_4$ alkyl)carbonylamino radical: —$N(R^t)(C=O)C_{1-4}$ alkyl, where $R^t$ is as defined above, and the alkyl group is also optionally mono-substituted by $R^q$ as defined above;
  (l) a ($C_1$-$C_4$ alkoxy) carbonylamino radical: —$N(R^t)(C=O)OC_{1-4}$ alkyl, where $R^t$ is as defined above, and the alkyl group is also optionally mono-substituted by $R^q$ as defined above;
  (m) a ureido group: —$N(R^t)(C=O)N(R^y)R^z$ where $R^t$, $R^y$ and $R^z$ are as defined above;
  (n) a sulfonamido group: —$N(R^t)SO_2R^s$, where $R^s$ and $R^t$ are as defined above;
  (o) a cyano group: —CN;
  (p) a formyl or acetalized formyl radical: —(C=O)H or —$CH(OCH_3)_2$;
  (q) ($C_1$-$C_4$ alkyl)carbonyl radical wherein the carbonyl is acetalized: —$C(OCH_3)_2C_{1-4}$ alkyl, where the alkyl is optionally mono-substituted by $R^q$ as defined above;
  (r) carbonyl radical: —$(C=O)R^s$, where $R^s$ is as defined above;
  (s) a hydroximinomethyl radical in which the oxygen or carbon atom is optionally substituted by a $C_1$-$C_4$ alkyl group: —$(C=NOR^z)R^y$ where $R^y$ and $R^z$ are as defined above, except they may not be joined together to form a ring;
  (t) a ($C_1$-$C_4$ alkoxy)carbonyl radical: —$(C=O)OC_{1-4}$ alkyl, where the alkyl is optionally mono-substituted by $R^q$ as defined above;
  (u) a carbamoyl radical: —$(C=O)N(R^y)R^z$ where $R^y$ and $R^z$ are as defined above;
  (v) an N-hydroxycarbamoyl or N($C_1$-$C_4$ alkoxy)-carbamoyl radical in which the nitrogen atom may be additionally substituted by a $C_1$-$C_4$ alkyl group: —$(C=O)$—$N(OR^y)R^z$ where $R^y$ and $R^z$ are as defined above, except they may not be joined together to form a ring;
  (w) a thiocarbamoyl group: —$(C=S)N(R^y)(R^z)$ where $R^y$ and $R^z$ are as defined above;
  (x) carboxyl: —$COOM^b$, where $M^b$ is as defined above;
  (y) thiocyanate: —SCN;
  (z) trifluoromethylthio: —$SCF_3$;
  (aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;
  (ab) an anionic function selected from the group consisting of: phosphono [P=O(OM$^b$)$_2$]; alkylphosphono {P=O(OM$^b$)—[O($C_1$-$C_4$ alkyl)]}; alkylphosphinyl [P=O(OM$^b$)—($C_1$-$C_4$alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where
    $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;
  (ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

(ad) $C_2$-$C_4$ alkenyl radical, optionally mono-substituted by one of the substituents (a) to (ac) above and phenyl which is optionally substituted by $R^q$ as defined above;

(ae) $C_2$-$C_4$ alkynyl radical, optionally mono-substituted by one of the substituents (a) to (ac) above;

(af) $C_1$-$C_4$ alkyl radical;

(ag) $C_1$-$C_4$ alkyl mono-substituted by one of the substituents (a)-(ac) above;

(ah) a 2-oxazolidinonyl moiety in which the point of attachment is the nitrogen atom of the oxazolidinone ring, the ring oxygen atom is optionally replaced by a heteroatom selected from —S— and $NR^t$ (where $R^t$ is as defined above) and one of the saturated carbon atoms of the oxazolidinone ring is optionally mono-substituted by one of the substituents (a) to (ag) above;

M is selected from:
(i) hydrogen;
(ii) a pharmaceutically acceptable esterifying group or removable carboxyl protecting group;
(iii) an alkali metal or other pharmaceutically acceptable cation; or
(iv) a negative charge which is balanced by a positively charged group.

DETAILED DESCRIPTION OF THE INVENTION

The manufacture of compounds of Formula I may be carried out in a three-stage synthesis scheme followed by a final step which allows for the removal of any protecting groups. The objective of the first synthetic stage is to produce a base phenanthrene compound which may be converted to the two-position substituent of the carbapenem of Formula I. The objective of the second synthetic stage is to attach the base phenanthrene to the carbapenem. Finally, the objective of the third synthetic stage is to substitute the phenanthrene with the desired $R^a$. This third synthetic stage may be performed after the first synthetic stage or during or after the second synthetic stage according to the nature of the various $R^a$.

Flow Sheet A demonstrates a suggested first stage synthesis. Flow Sheets B and C demonstrate two alternative second stage syntheses. The third synthesis varies according to the selected $R^a$.

The suggested first synthesis herein, Flow Sheet A, is generally known as a Pschorr Synthesis to produce phenanthrenes. This synthesis is described in P. H. Leake, Chem. Rev., 56 27 (1956); D. F. De Tar, Org. React., 9 409 (1957); E. A. Nodiff et. al., J. Med. Chem. 14 921 (1971); and E. A. Nodiff et. al., J. Med. Chem. 18 1011 (1975). These references are incorporated by reference. Other phenanthrene syntheses are described in A. J. Floyd, S. F. Dyke, and S. E. Ward, Chem. Rev., 76 509 (1976); F. B. Mallory and C. Mallory, Org. React. 30 1 (1984); G. Zanardi et. al., Synthesis 333 (1988); and V. Snieckus et. al., Tetrahedron Lett. 43 5459 (1988); also incorporated by reference.

Referring to Flow Sheet A, the 4-bromobenzo-aldehyde A1 is reacted in a Perkin Condensation with p-nitrophenylacetic acid A2 in acetic anhydride at about 40° C. using triethylamine as a catalyst. The resulting compound A3 contains a nitro group which can be reduced to an amine in order to close the phenanthrene ring. This is accomplished by heating compound A3 to about 100° C. in water with NaOH and $FeSO_4.7H_2O$ to produce compound A4, an amino-carboxylate. The amino-carboxylate A4 may be subsequently closed to phenanthrene A5 in a two-step reaction. Firstly, amino-carboxylate A4 is reacted with isoamyl nitrite and HCl in ethanol at about 0° C. Secondly, this reaction mixture is added to a suspension of copper in a solution of $NaH_2PO_2.H_2O$ and $H_2SO_4$ in water at about 40° C. The resultant phenanthrene A5 is the object compound of Flow Sheet A. It may be substituted with $R^a$ other than hydrogen as appropriate. However, using the starting materials shown, it must have carboxyl in the 9-position.

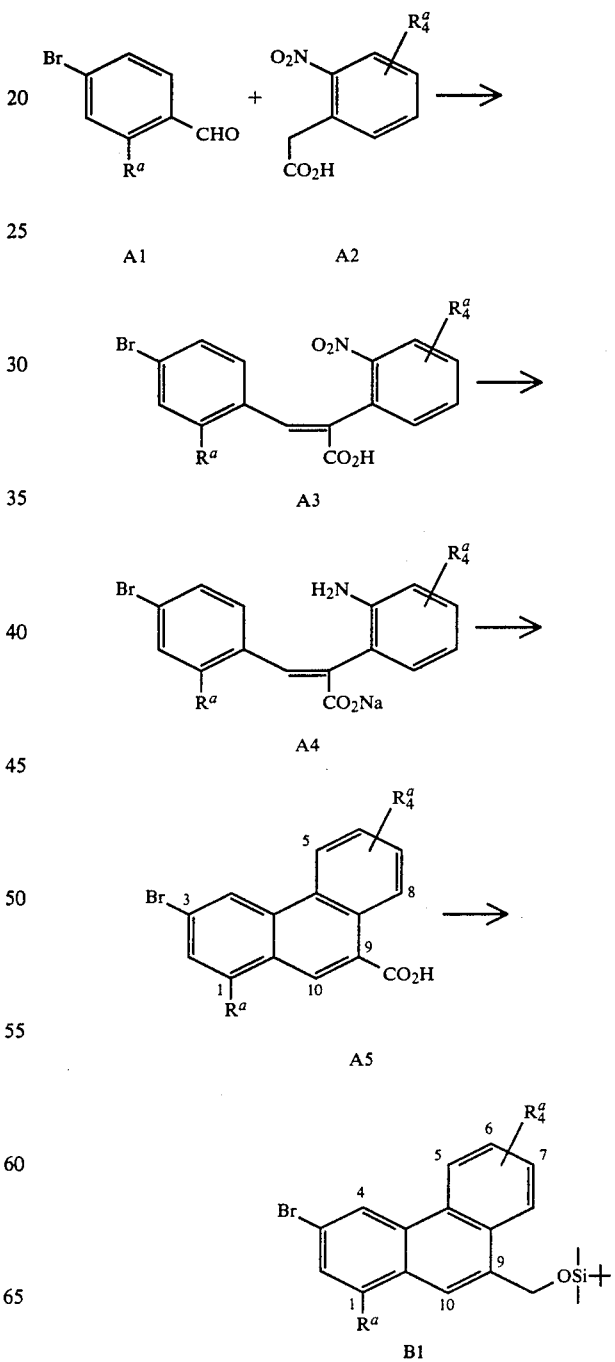

FLOW SHEET A

A simple variation of Flow Sheet A will produce a 10-position carboxyl substitution equivalent to compound A5. This variation requires that the fixed $R^a$ substitution and the bromine substitution of compound A1 be removed and placed on compound A2 with the bromine para to the acetic acid side-chain and meta to the nitro and to $R^a$. Of course the $R_4{}^a$ substitution of compound A2 should be placed on compound A1 leaving at least one position ortho to the aldehyde of A1 occupied by hydrogen. This interchange of substituents has the effect of rotating the phenanthrene to make what would have been the 9-position carbon of Flow Sheet A, the 10-position carbon and thus making the 9-position carboxyl substitution of Flow Sheet A, a 10-position carboxyl substitution.

The object compound of Flow Sheet A, phenanthrene A5, forms the nucleus of the 2-position substitution of the carbapenem compounds taught herein. As such it is shown to be $R^a$ substituted. However, it is immediately clear to those skilled in the art that certain $R^a$ listed above, if substituted on A1 or A2 or both would not survive or permit the synthesis to A5. Thus, where a certain $R^a$ is desired on the position-7 of compound A5 and this $R^a$ is not compatible with the synthesis scheme to produce A5, then a compatible precursor substituent may be employed through the synthesis.

The identity of the precursor substituent employed is not crucial so long as it does not interfere with the synthesis to A5 and so long as it may be thereafter converted to more desireable substitution. Preferred precursor substituents are methyl, hydroxymethyl and protected hydroxymethyl.

Thus, as to the $R^a$ substituent on compound A5, it may be an $R^a$ with or without protecting groups stable to the conditions of producing compound A5 and stable to the conditions of subsequently adding A5 to the carbapenem. Alternatively, it may be a stable precursor substituent which is stable to the conditions of making A5, which is optionally stable to the conditions of adding A5 to the carbapenem and which is convertible to a desired $R^a$ or to another precursor substituent.

Similarly to a precursor substituent, the 9- or 10-position carboxyl substitution of compound A5 may be employed to add the desired $R^a$ to these positions. Where an $R^a$ is desired in the 9- or 10-position, which is stable to the conditions of adding A5 to the carbapenem, then the carboxy may be replaced on A5 with this substitution by the appropriate chemistry. Where an $R^a$ is desired in the 9- or 10-position which is unstable to the chemistry of adding A5 to the carbapenem, then the carboxyl must be converted to a stable precursor substituent such as t-butyldimethylsilyloxy-methyl.

As stated above, the second stage synthesis is to attach the base phenanthrene to the 2-position of the carbapenem. Employing phenanthrene A5, a starting material B1 for the suggested second stage synthesis may be produced. Referring still to Flow Sheet A, and starting with A5, it is first necessary to convert the 9-position carboxyl to hydrogen, a desired $R^a$ substituent, or a precursor substituent thereto which is stable to the reaction conditions of adding the phenanthrene to a substituted azetidin-2-one precursor of the desired carbapenem. A t-butyldimethylsilyloxymethyl precursor substituent may be obtained on the 9-position of A5 in two steps. Firstly, carboxyl is reduced to hydroxymethyl by reacting A5 with borane in THF at 0° C. to RT. Secondly, the reaction product is isolated and reacted with t-butyldimethylsilyl chloride in dichloromethane with triethylamine and 4-dimethylaminopyridine to produce protected phenanthrene B1. With stable $R^a$ or suitable precursor substituents therefor, phenanthrene B1 may be added to azetidin-2-one B2 in a Grignard reaction as shown in Flow Sheet B. The Grignard reaction requires that B1 be converted to a Grignard reagent by reaction with magnesium and 1,2-dibromoethane in THF from 20° C. to 60° C. and subsequently contacting B1 as a Grignard reagent with B2 in THF at from −70° C. to about 20° C. to produce azetidin-2-one B3. Alternatively, B1 may be reacted with t-butyllithium, n-butyllithium, or the like in THF at from −78° C. to −50° C. followed by the addition of magnesium bromide to produce the same Grignard reagent. $R^i$ of B3 is in practice pyrid-2-yl but may clearly be a variety of substituents including aromatic and heteroaromatic substituents. Further $R^i$ might be for example phenyl, pyrimidinyl or thiazolyl.

Azetidin-2-one B3 is an intermediate that may be ring closed to a carbapenem. It is on this intermediate that $R^a$ or precursor substituent such as (t-butyldimethylsilyloxy)methyl may be modified where such modification is incompatible with the carbapenem nucleus. For example, a convenient reaction to remove the t-butyldimethylsilyl group of B3 is to expose it to a dilute solution of sulfuric acid in methanol at 0° C. for from a few minutes to several hours. Flow Sheet B shows the resulting compound B3A. If the t-butyldimethylsilyl group was removed under the same conditions after cyclization of B3 to a carbapenem, a substantial portion of the carbapenem would be degraded and lost. Thus, modification of the precursor substituent in this instance and replacement with another precursor substituent or even $R^a$ is best performed before closing the carbapenem. Of course it is possible to remove the t-butyldimethylsilyl group in reduced yield after cyclization of B3 to a carbapenem by reaction with tetra-n-butylammonium fluoride and acetic acid in THF.

Compound B3A may be ring closed to carbapenem B4 by refluxing in xylene with a trace of p-hydroquinone for about 1 to 2 hours in an inert atmosphere. It is on this intermediate that final elaboration of $R^a$ from a precursor substituent, e.g. hydroxymethyl, may be accomplished. Removal of the carboxyl and hydroxyl protecting groups then provides the final compound of Formula I. Such final elaboration and deprotection is described in further detail below.

FLOW SHEET B

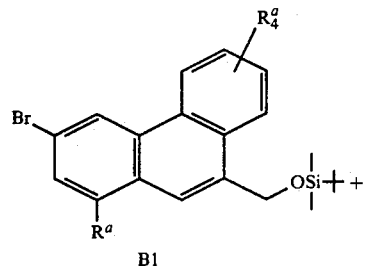

B1

-continued
FLOW SHEET B

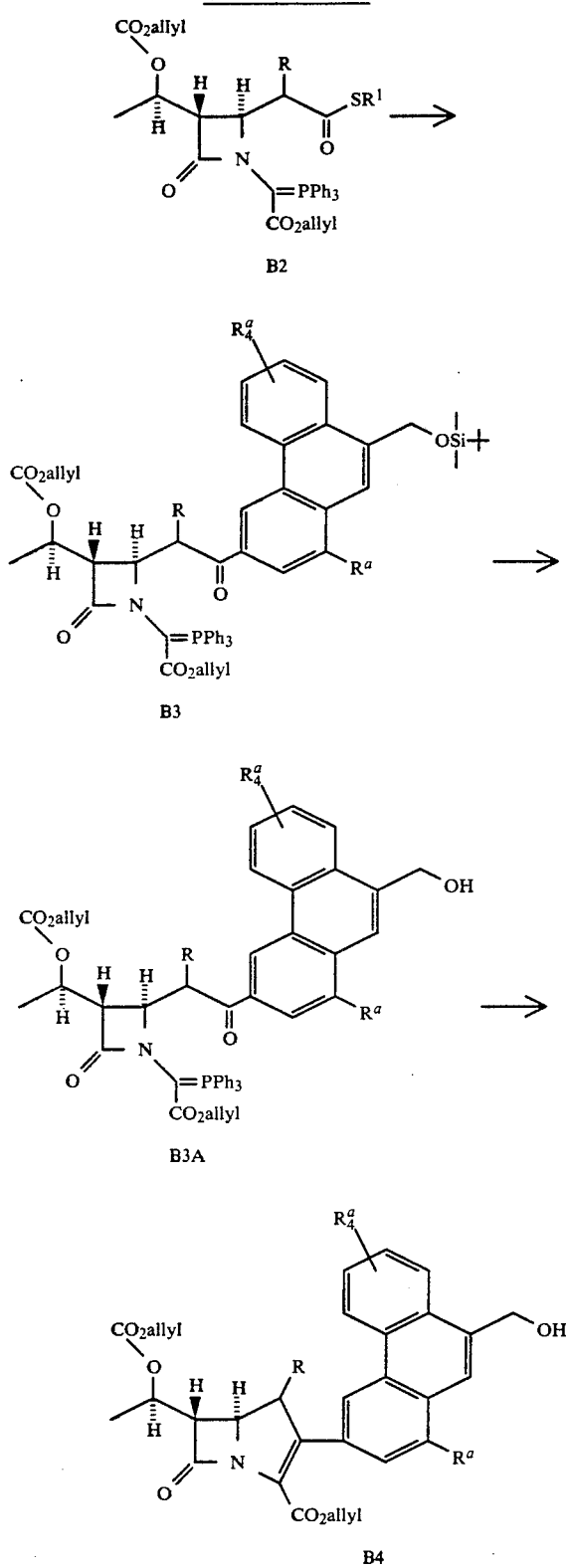

Flow Sheet C shows an alternative second stage synthesis, i.e. attachment of the base phenanthrene such as B1 to the 2-position of the carbapenem. This synthesis involves a palladium catalyzed cross-coupling reaction between a carbapenem triflate and a suitably substituted arylstannane, a process which is described in U.S. patent application Ser. No. 485,096 filed Feb. 26, 1990, hereby incorporated by reference. In order to apply this synthesis, it is first necessary to modify bromophenanthrene B1 to the trimethylstannylphenanthrene C3. This is accomplished by reacting B1 with t-butyllithium in THF at from −78° to −50° C. followed by the addition of trimethyltin chloride. This provides an intermediate from which the t-butyldimethylsilyl protecting group on the 9-position hydroxymethyl substituent is removed by exposure to tetra-n-butylammonium fluoride in THF yielding C3. Alternatively, bromophenanthrene B1 may be reacted with hexamethylditin in the presence of a palladium(0) catalyst such as tetrakis(triphenylphosphine)palladium in an inert solvent such as toluene at from 25° to 110° C. for from 0.25-24 hours to provide, after removal of the t-butyldimethylsilyl protecting group as described above, the same stannane C3. If the t-butyldimethylsilyl group was removed under the same conditions after attachment of the phenanthrene side chain to the carbapenem, a much reduced overall yield would be obtained due to degradation of the carbapenem during such removal. Thus modification of the precursor substituent in this instance and replacement with another precursor substituent or even $R^a$ is best performed before attachment to the carbapenem. Referring to Flow Sheet C, the 2-oxocarbapenam C1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in polar aprotic solvent, such as tetrahydrofuran or methylene chloride. An organic nitrogen base, such as triethylamine and the like, is then added to the reaction solution followed immediately by a silylating agent, such as trimethylsilyl trifluoromethanesulfonate to provide intermediate C2. An aprotic polar coordinating solvent, such as DMF, 1-methyl-2-pyrrolidinone and the like, is added. This is followed by the addition of a palladium compound, such as tris(dibenzylideneacetone)dipalladium-chloroform, palladium acetate and the like, a suitably substituted phenylphosphine, such as tris(4-methoxyphenyl)phosphine, tris(2,4,6-trimethoxyphenyl)phosphine and the like, and the stannane C3. A metal halide, such as lithium chloride, zinc chloride and the like, is added and the reaction solution is allowed to warm and is stirred at a suitable temperature, such as 0° to 50° C., for from a few minutes to 48 hours. The carbapenem C4 is obtained by conventional isolation/purification methodology known in the art.

Generally speaking, the milder conditions of the synthesis shown in Flow Sheet C allow for a wider range of functional groups $R^a$ to be present than the synthesis illustrated in Flow Sheet B. However, in certain cases it is advantageous for the $R^a$ substituent(s) of the stannane C3 to be introduced in a protected or precursory form. Final elaboration of $R^a$ from a precursor substituent, e.g. hydroxymethyl, may be accomplished on carbapenem intermediate C4. Removal of hydroxyl and carboxyl protecting groups then provides the final compound of Formula I. Such final elaboration and deprotection is described in further detail below.

FLOW SHEET C

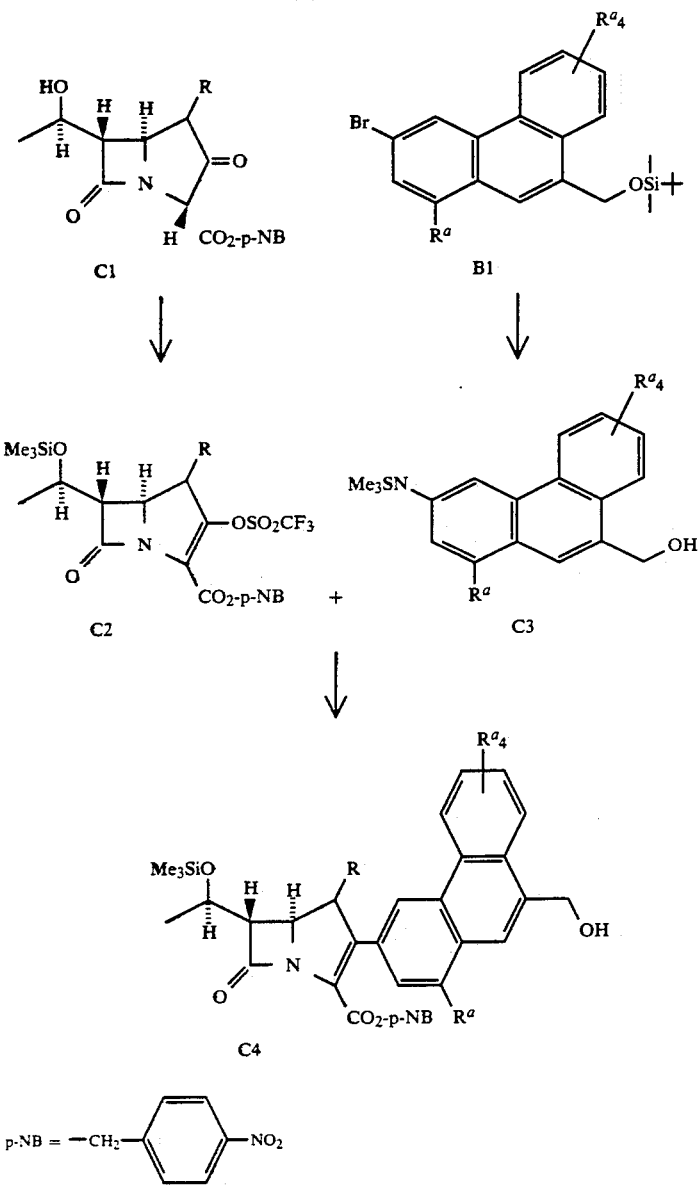

p-NB = —CH₂—⟨phenyl⟩—NO₂

Azetidin-2-one B2, a pyridyl-thioester, is a well known compound in the production of carbapenems. Diverse synthetic schemes useful to make B2 may be imagined by the skilled artisan. Particularly useful to the instant invention is a synthetic scheme set out further in Flow Sheet D below in which the symbol R is as defined above. The steps for preparing intermediate B2 are analogous to the procedures described, for example, in U.S. Pat. Nos. 4,260,627 and 4,543,257; L. D. Cama et al. *Tetrahedron* 39, 2531 (1983); R. N. Guthikonda et al. *J. Med. Chem.*, 30, 871 (1987) hereby incorporated by reference.

FLOW SHEET D

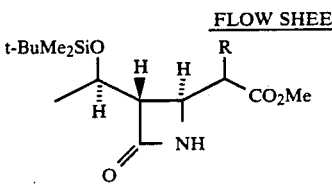

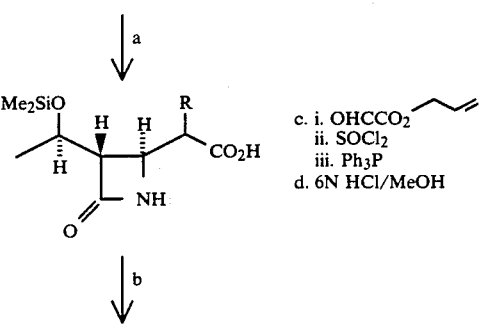

-continued
FLOW SHEET D

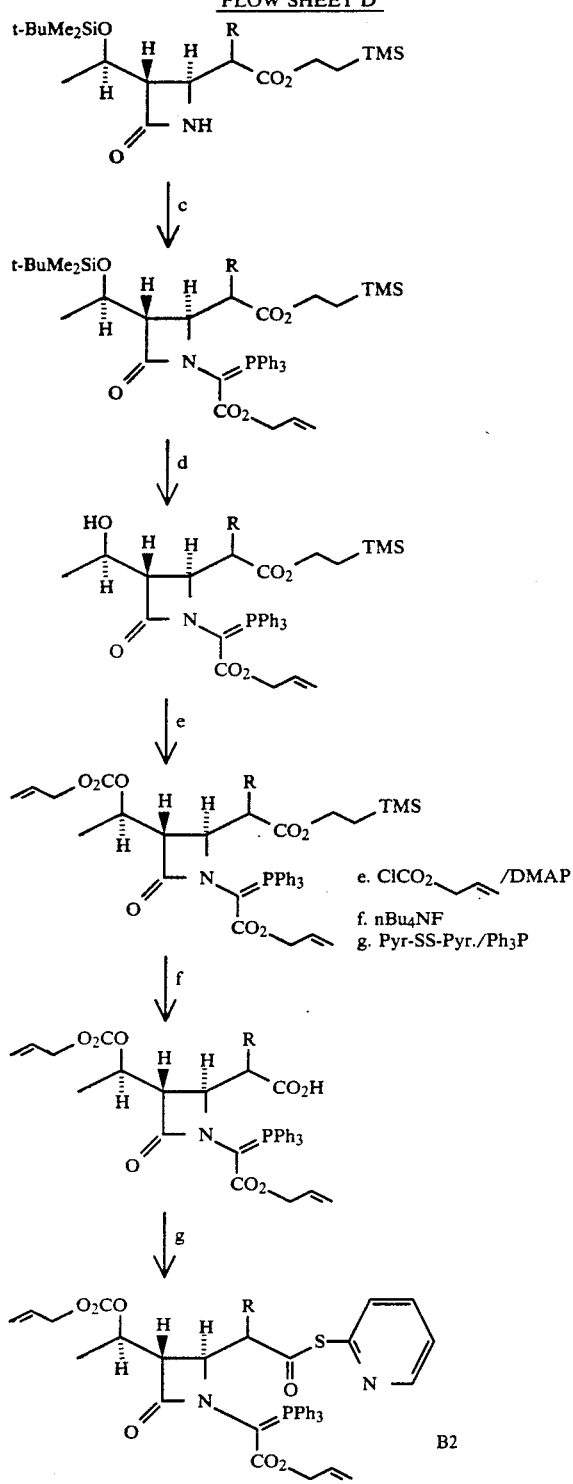

The steps for preparing the 2-oxocarbapenam intermediate C1 are well known in the art and are explained in ample detail by D. G. Melillo et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Company, Inc. and hereby incorporated by reference.

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanraku Ocean).

In the compounds of the present invention, one of the $R^a$ substituents must be of Type I. As a general matter, it is conjectured that anti-MSRA/MRCNS activity results from the configuration of the overall molecule uniquely conferred by the phenanthrene nucleus. The Type I substituent provides still greater anti-MRSA/MRCNS activity to the molecule.

The Type II $R^a$ substituents are distinguishable from Type I substituents chemically and with respect to the biological properties which they confer. In related compounds, it has been found that the Type II substituted compounds afford greater water solubility and reduced potential for CNS side effects. Substituents which tend to confer improved water solubility on the overall compound have been found useful, since they are contemplated to thereby improve the transport of the compound involved. Although a substantial number and range of Type II substituents have been described herein, all of these are contemplated to be a part of the present invention based on the biological performance of substituents related in terms of their medicinal chemistry.

Since it is possible to combine, in the compounds of the present invention, the required Type I substituents with the optional Type II substituents, there can be obtained a combination of desired attributes in the final overall molecule not attainable with a single substituent, i.e., improved anti-MRSA/MRCNS activity together with enhanced water solubility.

Type I substitutents employed in the compounds of the present invention may have quaternary nitrogen groups, and these include both cyclic and acyclic types, as is described under Type I. As already pointed out above, it is required that one, but no more than one, of the substituents $R^a$ must be a member selected from the group consisting of the definitions under Type I. It is optional that one, or at most three, of the remaining substituents may be a member selected from the group consisting of definitions under Type II. For example, $R^a$ at position 9- may be Type I and $R^a$ at position 1- may be of Type II, while the remaining substituents are hydrogen.

In preferred compounds of Formula I, $R^1$ is hydrogen. More preferably, $R^1$ is hydrogen and $R^2$ is (R)—$CH_3CH(OH)$— or (R)—$CH_3CH(F)$—. In the most preferred case, $R^1$ is hydrogen and $R^2$ is (R)—$CH_3CH(OH)$—. While R=H is usually preferred, there are instances in which R=$CH_3$ may provide improved chemical stability, water solubility, or pharmacokinetic behavior. The substituent R=$CH_3$ may be of either configuration, i.e., the α or β-stereoisomer. Additionally, in preferred compounds, at least one $R^a$ in the 1-, 9- or 10-postion of the phenanthrene is other than hydrogen. In the most preferred compounds, in total, up to two $R^a$ substituents in either the 1-, 9- or 10-positions are other than hydrogen.

Preferred Type I. (a) substituents include:

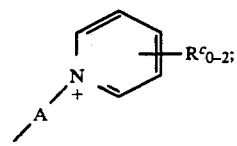

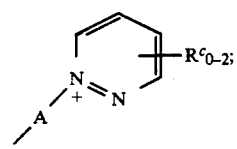

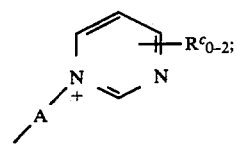

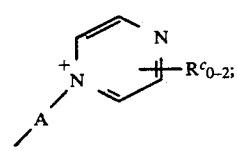

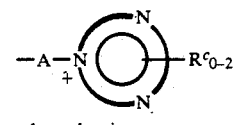

where the ring contains three carbon atoms;

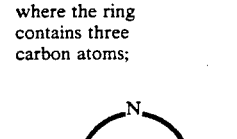

where the ring contains two carbon atoms;

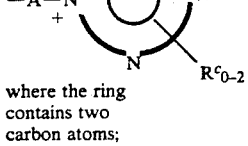

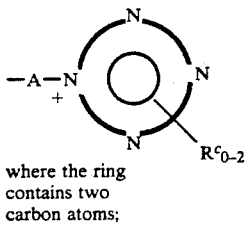

-continued

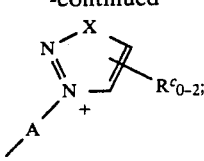

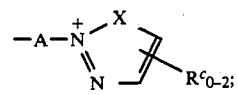

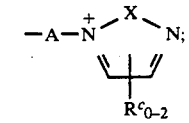

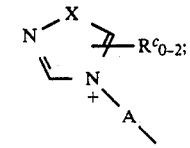

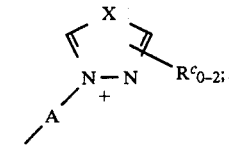

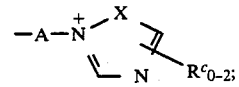

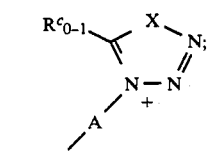

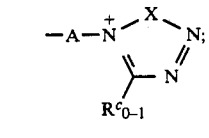

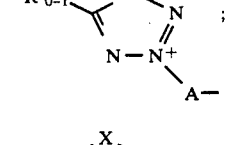

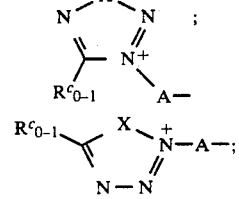

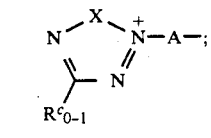

-continued
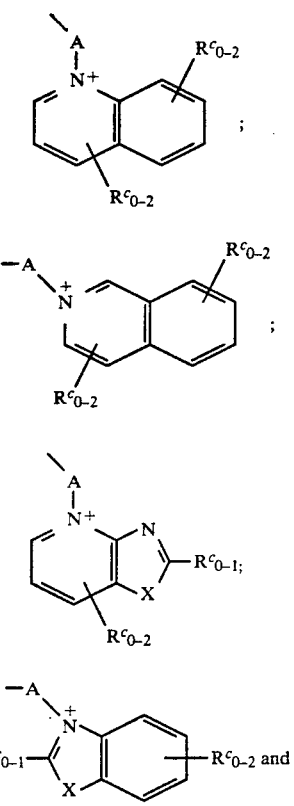
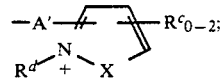
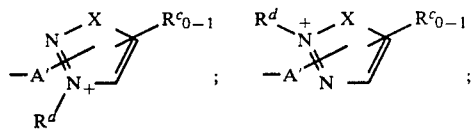
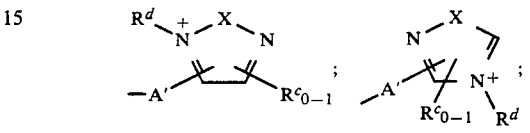
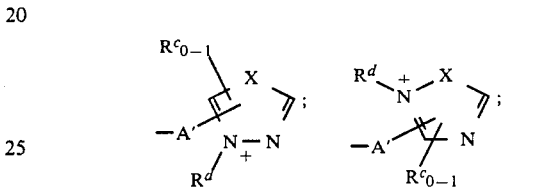
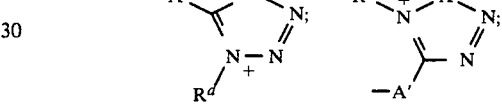
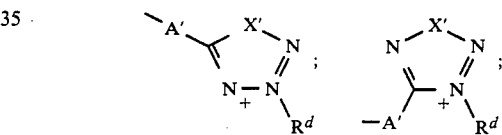
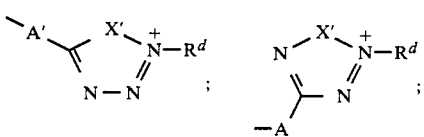
where X=O, S, or NR$^c$. For structures of Type I. (a), where R$^c$ is shown to have an indefinite position, it may be attached to any carbon of the ring.
Preferred Type I. (b) substituents include:
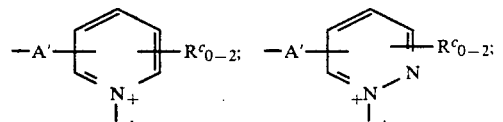
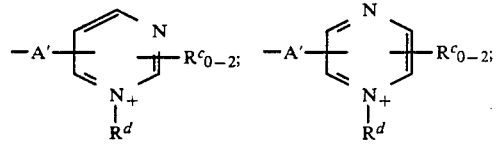
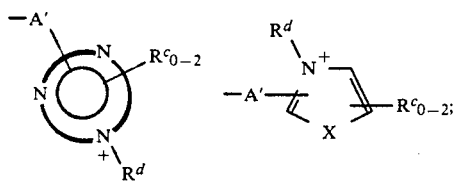
where the ring contains three carbon atoms;
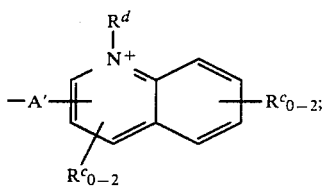
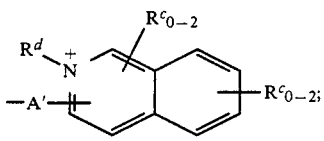
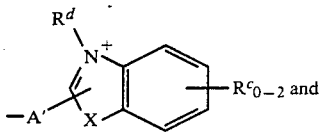

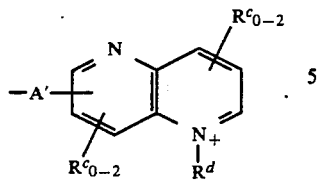

where X=O, S, or NR$^c$ and X'=O or S. For structures of Type I. (b), where R$^c$ and/or A' are shown to have indefinite positions, they are independently attached to any carbon atom of the ring.

Preferred Type I. (c) substituents include:

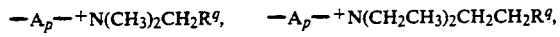

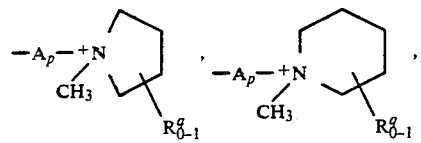

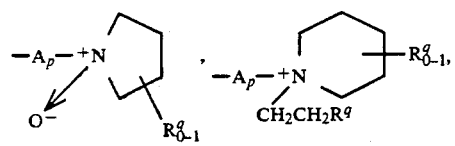

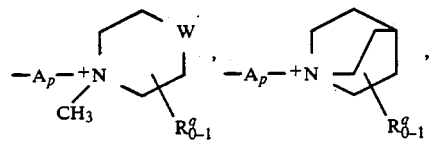

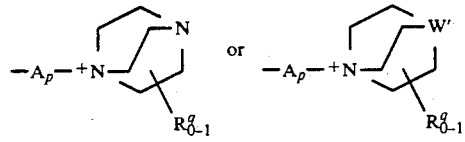

where W is O, S, NR$^e$, N(O)R$^e$, SO, SO$_2$ or N+(R$^e$)$_2$ and W' is N+R$^e$ or NO. For structures of Type I.(c), where R$^q$ is shown to have an indefinite position, it may be attached to any carbon atom of the ring.

Preferred Type I. (d) substituents include:

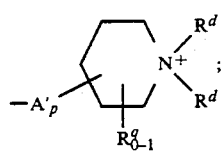

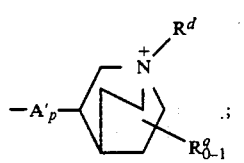

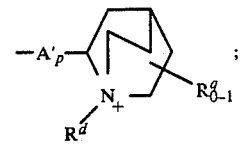

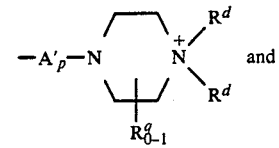

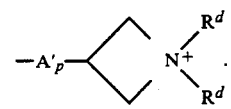

For structures of Type I.(d), where R$^q$ and/or A'$_p$ is shown to have an indefinite position, it may be attached to any carbon atom of the ring.

The R$^c$ substituents herein are intended to represent suitable further substituents on the Type I. (a) or (b) substituents for the phenanthrenyl ring. As seen above, these Type I. (a) or (b) substituents are monocyclic or bicyclic aromatic groups containing heteroatoms. Given this class of primary substituent, further suitable substituents may be readily discovered in the penem and carbapenem art. For example, suitable substituents for Type I. (a) or (b) substituents are generally taught in U.S. Pat. No. 4,729,993 assigned to Merck and Co. or in U.S. Pat. No. 4,746,736 assigned to Bristol-Myers Co. These patents are hereby incorporated by reference.

Broadly, R$^c$ may be the same or different and may be selected on an independent basis from the group as defined above. While a single such substitution is preferred, there is occasion to use up to two such substituents on an R$^a$, e.g., where it is desired to enhance the effect of a particular substituent group by employing multiple substituents. The particular choice of R$^c$ will depend upon the situation. For instance, a specific R$^c$ may lend particular stability to a nitrogen cation. At other times it may be desired to employ a substituent known to enhance antibacterial activity of the overall molecule against a particular bacterium, for example, while also employing a substituent known to improve some other property such as water solubility or the duration of action of the overall molecule.

The scope of R$^c$ herein includes two specific Types of further substituent attached to the Type I. (a) or (b) substituent. A first Type of R$^c$ are those attached to a ring carbon and a second Type of R$^c$ are those attached to a neutral ring nitrogen. Persons skilled in the art will readily recognize that a wide range of organic substituents are suitably used as R$^c$. Persons skilled in the art will also recognize that some substituents including the —NR$^y$R$^z$ substituents, useful for one purpose of R$^c$, i.e. carbon substitution, are not equally useful in the other, i.e. nitrogen substitution.

Preferred R$^c$ attached to ring carbon atoms are —NH$_2$, —SCH$_3$, —SOCH$_3$, —CH$_2$OH, —(CH$_2$)$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, CH$_2$CH$_3$, CH$_2$CONH$_2$ and CH$_2$CON(C$_1$-C$_4$alkyl) where M$^b$ is defined above. Preferred R$^c$ attached to neutral ring nitrogen atoms are —CH$_2$OH, —(CH$_2$)$_2$OH, —CH$_2$COOM$^b$, —CH$_2$CH$_2$COOM$^b$, —CH$_2$SOCH$_3$, —CH$_2$SCH$_3$, —CH$_2$SO$_3$M$^b$, —CH$_2$CH$_2$SO$_3$M$^b$, —CH$_3$, CH$_2$CH$_3$, CH$_2$CONH$_2$ and CH$_2$CON(C$_1$-C$_4$alkyl) where M$^b$ is defined above.

It is preferred that each Type I. (a) or (b) substituent have no more than two R$^c$ substituents which are other than hydrogen. Thus, the formula shown above for Type I. (a) substituents has up to two R$^c$ substituents with the remainder of course being hydrogen. Further, the formula for the Type I. (b) substituent also allows up to two R$^c$. In accordance with these formulae, the previously listed more specific structures should be interpreted to have no more than two R$^c$ for each monocyclic or bicyclic group. Similarly for Type I. (c) or (d) substituents it is preferred that any monocylic or bicyclic group have no more than a single R$^q$ substituent.

The scope of R$^d$ includes a single type of further substituent attached a Type I. (b) or (d) substituent. The R$^d$ substituents are attached to a cationic nitrogen which may or may not be aromatic. Preferred R$^d$ attached to cationic nitrogen atoms are hydrogen, —CH$_3$, CH$_2$CH$_3$, —CH$_2$CH$_2$CH$_3$, —CH$_2$COOM$^b$, —CH$_2$SO$_3$M$^b$, —NH$_2$ and O$^{(-)}$, where M$^b$ is defined above.

The formulas depicting Type Ib, Ic, and Id substituents show positively charged states for those substituents. It is understood that certain of those substituents, which are cationic by virtue of having a protonating hydrogen atom attached to the nitrogen, may also exist or be produced under certain conditions as a neutral substituent by virtue of the absence of such a hydrogen atom (ie. in Type Ib, when there is no R$^d$; in Type Ic, when there is no R$^w$; and in Type Id, when there is zero to one R$^d$, depending on Type of heterocycle). Whether such a Type Ib, Ic, or Id substituent will be predominately cationic or neutral in a given physical state will be governed by principles of acid-base chemistry, which are well known to those skilled in the art. For example, the particular ratio of neutral form to cationic form will depend upon the basicity of the amine and acidity of a solution. When such a substituent is in a protonated quaternized state, the compound exists as a zwitterion which is internally balanced as to charge or as an ammonium salt which is externally balanced. In illustration, if there is no R$^d$ on a Type Ib substituent, it is understood that such a substituent is neutral (there is no positive charge on the nitrogen). A compound containing such a substituent is typically produced in this form as a salt, wherein M is an alkali metal, and may exist in solution in its neutral form. However, depending upon conditions, a compound containing a neutral Type Ib substituent may be in equilibrium with, and may also be represented by a formula showing, the corresponding compound containing the quaternized protonated substituent where R$^d$ is present and is a hydrogen atom. Furthermore the same compound may exist with the Type Ib substituent in a completely protonated quaternized form, for instance in an aqueous solution in the presence of a stoichiometric amount of a strong mineral acid. It is intended herein that both the protonated (cationic) and the unprotonated (neutral) forms of Type Ib, Ic and Id substituents of the type just described are within the scope of the present invention.

Suitable A spacer moieties include —CH$_2$—, —CH$_2$CH$_2$—, —CH$_2$CH$_2$CH$_2$—, —CH$_2$CH$_2$CH$_2$CH$_2$—, —OCH$_2$CH$_2$—, —SOCH$_2$—, —SO$_2$CH$_2$—, —SCH$_2$CH$_2$—, —SOCH$_2$CH$_2$—, —SO$_2$CH$_2$CH$_2$—, —NHCH$_2$CH$_2$—, —N(CH$_3$)CH$_2$CH$_2$—, —CH$_2$N(CH$_3$)CH$_2$CH$_2$—, —CONHCH$_2$CH$_2$—, —SO$_2$NHCH$_2$CH$_2$—, —COCH$_2$—, —CH=CHCH$_2$— and —CH$_2$OCH$_2$CH$_2$—. Preferably, where Q is O, S, NH or N(C$_{1-4}$alkyl), then n is 2-6.

Suitable A' are listed for A above. Further A' may suitably be —O—, —S—, —NH—, —SO$_2$—, —SO$_2$NH—, —CONH—, —CH=CH—, —CH$_2$S—, —CH$_2$NH—, —CONHCH$_2$— or —SO$_2$NHCH$_2$—.

The Type I. cationic substituents are generally added to the phenanthrene following attachment of the phenanthrene to the carbapenem. Conveniently, the phenanthrene side-chain should be synthesized with a precursor substituent which may be elaborated into the desired cationic substituent. The identity of the precursor substituent will vary according to the particular R$^a$ desired. For example, one such precursor substituent is —A—OH, such as hydroxymethyl.

The hydroxymethyl precursor substituent may be elaborated into cationic substituents of Type I. (a) by converting the hydroxyl into an active leaving group such as an iodide (giving —A—I) followed by reaction with a desired nitrogen containing aromatic compound. More particularly, two alternative procedures may be utilized to produce a leaving group on the moiety —A— and subsequently to replace such a leaving group with cationic substituents of the type just described.

For a first procedure, the hydroxyl group of —A—OH may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate may converted to the reactive iodide derivative by treatment with sodium iodide in a suitable solvent, e.g., acetone, at reduced or ambient temperatures. Alternatively, the hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. Once the iodide has been formed, the introduction of the cationic substituent is accomplished simply by treating the iodide with the desired nitrogen containing compound, e.g. a heteroaromatic compound such as pyridine. The reaction will proceed in a suitable solvent, such as acetonitrile, at or about room temperature. This displacement reaction may also be facilitated by the addition of excess silver trifluoromethanesulfonate to the reaction mixture, in which case reduced temperatures are often desireable.

For a second procedure, the hydroxyl group of —A—OH may be converted into the reactive trifluoromethanesulfonate (triflate) group. However, such an activating group cannot be isolated by conventional techniques but may be formed and used in situ. Thus, treatment of the hydroxyl group with trifluoromethanesulfonic (trific) anhydride in the presence of a hindered, non-nucleophilic base such as 2,6-lutidine, 2,4,6-collidine, or 2,6-di-tert-butyl-4-methylpyridine in a suitable solvent, such as dichloromethane, at reduced temperatures provides for the generation of the triflate activating group. Introduction of the cationic group is then accomplished by reacting the above triflate in situ with the desired nitrogen containing compound at reduced temperature. In certain cases it is possible and desireable to use the reacting nitrogen containing compound as the base for the formation of the triflate activating group. In this case treatment of the hydroxyl group with triflic anhydride in the presence of at least two equivalents of the reacting nitrogen compound under the conditions described above provides the cationic substituent.

Where the cationic substitution has a substituent $R^c$, the most facile method of providing such a substituent is to employ as the reactant in the preparation methods described above a nitrogen containing compound which already has the desired substituent. Such substituted compounds are readily available starting materials or may be prepared in a straight-forward manner using known literature methods.

The Type I. (b) cationic substituents are prepared by quaternization of an aromatic ring nitrogen of a neutral precursor substituent on the phenanthrene ring. Examples of neutral precursor substituents are —CONHCH$_2$—(2-pyridyl), —CONHCH$_2$—(4-pyridyl) or —SO$_2$CH$_2$—(4-pyridyl). Quaternization is accomplished by reacting the nitrogen compound in an inert organic solvent (e.g.CH$_2$Cl$_2$) at about 0° C. to room temperature with an alkylating agent $R^d$—Y where $R^d$ is given above and Y is a leaving group such as iodide, bromide, mesylate (methanesulfonate), tosylate (p-toluenesulfonate) or triflate. Alternatively, the aromatic ring nitrogen may be quaternized by reaction with an oxidizing agent such as 3-chloroperbenzoic acid (giving the N-oxide) or an amidinating reagent such as o-(2,4,6-triisopropylbenzenesulfonyl)hydroxylamine (giving the N-amino derivative) in a suitable solvent (e.g. dichloromethane or CH$_3$CN) at about room temperature. In addition, the neutral precursor substituent may be rendered cationic through protonation of the basic aromatic ring nitrogen. This may be accomplished by treatment of the neutral precursor with a suitable inorganic or organic acid, e.g. hydrochloric acid, phosphoric acid, hydrobromic acid, acetic acid or benzoic acid. Protonation may further be accomplished by a carboxylic acid function elsewhere in the molecule, including the C—3 carboxyl on the carbapenem. The neutral precursor substituent may be already attached to the phenanthrene ring at the time of its connection to the carbapenem, or it may be elaborated from a simpler precursor after connection to the carbapenem. An example of a precursor substituent for elaboration is —A-'—OH such as hydroxymethyl. In one suggested synthesis, the hydroxyl may be converted to a reactive leaving group such as iodo as described above. The iodide is then reacted in a nucleophilic displacement reaction with a nitrogen containing aromatic compound which has a nucleophilic side-chain substituent such as CH$_2$SH or CH$_2$NH$_2$. In this displacement reaction, it is the side-chain substituent that is the reacting nucleophile and not the aromatic ring nitrogen. Suitable substrates for this reaction include 2-(mercaptomethyl)-pyridine, 2-aminopyridine, 2-(aminomethyl)pyridine or 4-(mercaptomethyl)pyridine. The reaction is carried-out in an inert organic solvent, e.g. methylene chloride, at from about 0° C. to room temperature in the presence of a non-nucleophilic base such as triethylamine or diisopropylethylamine. Quaternization or protonation of the aromatic ring nitrogen as described above then gives the Type I.b) cationic substituent. A second suggested synthesis of a Type I.b) cationic substituent starting from a precursor —A'—OH (e.g. hydroxymethyl) consists of oxidation of the alcohol functionallity to an aldehyde followed by Wittig-type olefination with an appropriate nitrogen-containing aromatic substituted reagent, and finally quaternization. The oxidation may be conveniently accomplished by a Swern oxidation employing oxalyl chloride-dimethylsulfoxide followed by triethylamine. The reaction is conducted in methylene chloride as a solvent at from −70° C. to 0° C. The Wittig reaction is carried-out by reacting the aldehyde with the desired Wittig reagent in a polar solvent such as acetonitrile or dimethylsulfoxide at about room temperature. Suitable Wittig reagents include: pyridylmethylenetriphenylphosphorane, quinolylmethylenetriphenylphosphorane, and thiazolylmethylenetriphenylphosphorane. Quaternization or protonation as described above then completes the synthesis of the Type I. (b) cationic substituent. Depending on the particular $R^a$ of Type I. (b) that is desired, many other synthesis schemes may be employed, as would be apparent to an organic chemist skilled in the art.

The Type I. (c) cationic substituents may be prepared in an analogous manner to that described for I. (a) substituents except that the nitrogen containing compound employed in the displacement reaction is an aliphatic amine (i.e. NR$^y$R$^z$R$^w$). However, in cases where the amino group is directly bonded to the phenanthrene nucleus (i.e. —A$_p$N$^+$R$^y$R$^z$R$^w$ where p=0) the amine is most conveniently attached to the phenanthrene prior to its incorporation into the carbapenem system. If such an amine is primary or secondary, it may require protection with a suitable amine protecting group during the steps employed to attach the phenanthrene to the carbapenem. Tertiary amines require no protection and may be quaternized or protonated as described for the Type I.b) cationic substituents.

The Type I. (d) cationic substituents are prepared by quaternization or protonation of a non-aromatic ring nitrogen of an appropriate neutral precursor substituent on the phenanthrene ring. Quaternization or protonation is accomplished as described above for the Type I. (b) substituents. As with the Type I. (b) substituents, the neutral precursor may already be attached to the phenanthrene ring at the time of its connection to the carbapenem, or the neutral precursor may be elaborated from a simpler precursor substituent on the phenanthrene ring after its connection to the carbapenem. Examples of neutral precursor substituents are: —CONH(3-quinuclidinyl), —CONH[4-(N-methylpiperidinyl)], —SO$_2$CH$_2$CH$_2$[2-(N-methylpyrrolidinyl)], —SO$_2$NH[1-(4-methylpiperazinyl)] and —CH$_2$[1-(4-methylpiperazinyl)]. Elaboration of the neutral precursor substituent from a simpler substituent such as hydroxymethyl may be accomplished in an analogous manner to that described previously for the Type I. (b) substituents by employing appropriate reagents to introduce the Type I. (d) non-aromatic ring nitrogen moiety which is subsequently to be quaternized or protonated.

Among preferred $R^a$ of Type II are $C_{1-4}$ alkyl monosubstituted with hydroxy, such as, hydroxymethyl; formyl; carboxy, such as, —COOK; carbamoyl, such as, —CONH$_2$; hydroximinomethyl, such as, —CH=NOH or cyano.

In regard to this preferred substitution, the hydroxymethyl groups may be obtained in the 9-and 10-positions of the phenanthrene as shown in Flow Sheets A and B. The hydroxymethyl may be obtained in any of positions 1, 5, 6, 7 or 8 as follows. Methyl, as a precursor substitutent, is substituted on starting materials A1 and-/or A2 in the appropriate positions by well know means and the starting materials reacted to a corresponding methyl-substituted A5 according the Flow Sheet A. At this point, the 9- or 10-position carboxy may be removed from methyl-substituted A5, if desired, by heating with copper powder or a copper salt, such as, $CuCO_3$ in a high boiling solvent, such as, quinoline. Subsequently, the methyl substituent of methyl-substituted A5 may be oxidized e.g. to carboxy with chromium trioxide or to bromomethyl with N-bromosuccinimide. This oxidation of the precursor substituent, methyl, is advantageously performed prior to substituting the phenanthrene on the azetidin-2-one as the oxidizing conditions are incompatible with either the azetidin-2-one or the subsequent carbapenem. The resultant 1, 5, 6, 7 or 8 carboxy or bromomethyl substituted phenanthrene may be further elaborated to obtain a corresponding "isomeric" B1. In the case of the carboxy substituent, this is accomplished as previously described in Flow Sheet A. In the case of the bromomethyl substituent, conversion to an isomeric B1 may be accomplished by a three-step sequence. Reaction of the bromomethyl compound with potassium acetate in DMF at 80° C. gives the corresponding acetoxymethyl compound. Removal of the acetate group, e.g. by hydrolysis with methanolic sodium hydroxide or by reduction with diisobutylaluminium hydride in THF, gives the hydroxymethyl substituted compound which is converted to the isomeric B1 by silylation with t-butyldimethylsilyl chloride, triethylamine and 4-dimethylaminopyridine in dichloromethane. Further elaboration of isomeric B1 according to Flow Sheet B produces a corresponding isomeric B3, B3A and B4. Of course, the isomeric B4 is the hydroxymethyl of the 1, 5, 6, 7 or 8 positions sought above.

The preferred formyl substitution on the phenanthrene may be obtained from the hydroxymethyl substitution of B4 or isomeric B4 just described by a Swern oxidation. For example, isomeric B4 is oxidized in methylene chloride at from $-70°$ C. to room temperature employing oxalyl chloride-dimethyl sulfoxide followed by triethylamine as the active agent. Obviously, the position of the resultant formyl substitution will depend upon the position of the hydroxymethyl substitution in isomeric B4.

The preferred —CH=NOH substitution on the phenanthrene may be conveniently obtained from the formyl substitution just described. This is accomplished simply by exposing the formyl substituted compound to hydroxylamine in an appropriate solvent at room temperature.

The preferred cyano substitution on the phenanthrene may be obtained from the —CH=NOH substitution just described. The —CH=NOH substituted compound is dehydrated with triflic anhydride and triethylamine in a solvent at $-70°$ C.

The preferred —COOK substitution on the phenanthrene may be obtained from the hydroxymethyl substituted B3A or isomeric B3A described above. For example, an isomeric B3A is oxidized with Jones reagent to convert the hydroxymethyl substituent to the carboxylic acid group. The oxidation with Jones reagent may be incompatible with the carbapenem and thus is optimally performed before ring closure. Prior to ring closure, the carboxylic acid group is protected as its allyl ester to permit cyclization of the carbapenem. Protection is carried out by alkylating with allyl bromide and triethylamine. Deprotection following cyclization is carried out in a palladium catalyzed reaction, in a solution containing potassium 2-ethylhexanoate as described in McCombie and Jeffrey, *J. Org. Chem.*, 47, 2505 (1983). Deprotection in such a solution yields the desired potassium salt.

The preferred carbamoyl substitution on the phenanthrene may be obtained from B3A or "isomeric" B3A by oxidizing the hydroxymethyl group with Jones reagent to the corresponding carboxylic acid group as described above. This carboxylic acid substituent is converted to the carboxamide group, $-CONH_2$, by sequentially contacting with 1-ethyl-3-(3-dimethylaminopropyl)-carbodiimide hydrochloride, 1-hydroxybenzotriazole, and ammonia in an organic solvent at room temperature. Substituted amides may of course be obtained by replacing ammonia with the corresponding substituted amine. In contrast to the carboxyl substitution, this carbamoyl group requires no protection for the conditions of carbapenem cyclization.

Compounds substituted with the preferred $R^a$ of Type II just described may also be obtained by employing the synthesis shown in Flow Sheet C. In this case, the synthetic transformation just described may be carried-out on intermediate C3 prior to attachment of the phenanthrene side chain to the carbapenem or on C4 after such attachment.

In addition to or including the above, suitable $R^a$ of Type II include:

| | |
|---|---|
| $-OCH_3$ | $-OCH_2CO_2Na$ |
| $-OCH_2CH_2OH$ | $-CF_3$ |
| $-F$ | $-Cl$ |
| $-Br$ | $-I$ |
| $-OH$ | $-OCOCH_3$ |
| $-OCONH_2$ | $-SCH_3$ |
| $-SOCH_3$ | $-SO_2CH_3$ |
| $-SCH_2CH_2OH$ | $-SOCH_2CH_2OH$ |
| $-SO_2NH_2$ | $-SO_2N(CH_3)_2$ |
| $-NHCHO$ | $-NHCOCH_3$ |
| $-NHCO_2CH_3$ | $-NHSO_2CH_3$ |
| $-CN$ | $-CHO$ |
| $-COCH_3$ | $-COCH_2OH$ |
| $-CH=NOH$ | $-CH=NOCH_3$ |
| $-CH=NOCH_2CO_2H$ | $-CH=NOCMe_2CO_2H$ |
| $-CH=NOCMe_2CO_2Me$ | $-CO_2CH_2CH_2OH$ |
| $-CONH_2$ | $-CONHCH_3$ |
| $-CON(CH_3)_2$ | $-CONHCH_2CN$ |
| $-CONHCH_2CONH_2$ | $-CONHCH_2CO_2H$ |
| $-CONHOH$ | $-CONHOCH_3$ |
| $-$tetrazolyl | $-CO_2Na$ |
| $-SCF_3$ | $-PO_3NaH$ |
| $-CONHSO_2Ph$ | $-CONHSO_2NH_2$ |
| $-SO_3Na$ | $-SO_2NHCN$ |
| $-SO_2NHCONH_2$ | $-CH=CHCN$ |
| $-CH=CHCONH_2$ | $-CH=CHCO_2Na$ |
| $-C\equiv C-CONH_2$ | $-C\equiv C-CN$ |
| $-CH_2OH$ | $-CH_2N_3$ |
| $-CH_2CO_2Na$ | $SO_2CH_2CH_2OH$ and $-CH_2I$. |

In the preparation methods described above, the carboxyl group at the 3-position and the hydroxyl group at the 8-position of the carbapenem remain blocked by protecting groups until the penultimate product is prepared. Deblocking may be carried out in a conventional manner. For compounds prepared according to Flow Sheet B, deprotection may be carried out in a palladium catalyzed reaction in a solution containing potassium 2-ethylhexanoate and 2-ethylhexanoic acid or, alternatively, another suitable nucleophile such as pyrrolidine. Alternatively, for those prepared via Flow Sheet C, deprotection is conducted sequentially. Thus, compound C4 is exposed initially to aqueous acidic conditions, acetic acid or dilute HCl or the like, in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as NaHCO$_3$ or KHCO$_3$ and 10% Pd/C followed by hydrogenation provides for the removal of the p-nitrobenzyl protecting group and the formation of the final compound of Formula I.

The overall molecule must be electronically balanced. Since a quaternary nitrogen is present in the compounds of the present invention, a balancing anion must also, in that case, be present. This is usually accomplished by allowing COOM to be COO$^-$. However, where M is, e.g., a pharmaceutically acceptable ester, a counterion (anion) Z$^-$ must be provided, or alternatively, an anionic substituent might be utilized. A counterion must also be provided or additional anionic substituent utilized where there is more than one quaternary nitrogen. Further, it is within the scope of this invention to utilize an anionic substituent where the quaternary nitrogen is already balanced by COOM= COO$^-$. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

The term "quaternary nitrogen" as used herein refers to a tetravalent cationic nitrogen atom including the cationic nitrogen atom in a tetra-alkylammonium group (e.g. tetramethylammonium, N-methylpyridinium), the cationic nitrogen atom in a protonated ammonium species (e.g. trimethyl-hydroammonium, N-hydropyridinium), the cationic nitrogen atom in an amine N-oxide (e.g. N-methylmorpholine-N-oxide, pyridine-N-oxide), and the cationic nitrogen atom in an N-amino-ammonium group (e.g. N-aminopyridinium).

The term "heteroatom" means N, S, or O, selected on an independent basis.

The term "heteroaryl" has been defined herein, in relation to the R$^x$ group, to have a specific and limited meaning, being only monocyclic. While the cationic groups I. (a) and (b) also clearly include heteroaryl groups, being both monocyclic and bicyclic, the term "heteroaryl" has not been used in association with the definitions of those cationic groups above. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1N+1 O or 1 S). While additional nitrogen atoms may be present together with the first nitrogen and oxygen or sulfur, giving, e.g., a thiadiazole (2N's=1 S), the preferred heteroaryls are those where *only* nitrogen heteroatoms are present when there is more than one. Typical of these are pyrazole, imidazole, pyrimidine and pyrazine (2N's) and triazine (3N's).

The heteroaryl group of R$^x$ is always optionally mono-substituted by R$^q$, defined above, and substitution can be on one of the carbon atoms or one of the heteroatoms, although in the latter case certain substitutent choices may not be appropriate.

Listed in Table I are specific compounds of the instant invention:

TABLE I

| M | R$^a$ | R$^a$ Position |
|---|---|---|
| (−) | −CH$_2$N$^+$(pyridyl)NH$_2$ | 1 |
| (−) | −CH$_2$N$^+$(pyridyl)NH$_2$ | 7 |
| (−) | −CH$_2$N$^+$(pyridyl)NH$_2$ | 8 |
| (−) | −CH$_2$N$^+$(pyridyl)NH$_2$ | 9 |
| (−) | −CH$_2$N$^+$(pyridyl)NH$_2$ | 10 |
| (−) | −CH$_2$N$^+$(pyridyl)-NH$_2$ | 1 |
| (−) | −CH$_2$N$^+$(pyridyl)-NH$_2$ | 7 |
| (−) | −CH$_2$N$^+$(pyridyl)-NH$_2$ | 8 |
| (−) | −CH$_2$N$^+$(pyridyl)-NH$_2$ | 9 |

TABLE I-continued

| | | |
|---|---|---|
| (−) | −CH₂N⁺(pyridine-4-NH₂) | 10 |
| (−) | −CH₂N⁺(imidazole-N−CH₃) | 1 |
| (−) | −CH₂N⁺(imidazole-N−CH₃) | 7 |
| (−) | −CH₂N⁺(imidazole-N−CH₃) | 8 |
| (−) | −CH₂N⁺(imidazole-N−CH₃) | 9 |
| (−) | −CH₂N⁺(imidazole-N−CH₃) | 10 |
| (−) | −CH₂N⁺(1,2,4-triazole-N−CH₃) | 9 |
| (−) | −CH₂N⁺(1,2,4-triazole-N−CH₃) | 9 |
| (−) | −CH₂N⁺(imidazole-NCH₂CONH₂) | 9 |
| (−) | −CH₂N⁺(pyrazoline-N−CH₃) | 9 |
| (−) | −CH₂N⁺(imidazole-N−CH₂SOCH₃) | 9 |
| K | −CH₂N⁺(imidazole-NCH₂SO₃⁻) | 9 |
| K | −CH₂N⁺(imidazole-NCH₂CO₂⁻) | 9 |
| K | −CH₂N⁺(pyridine-4-CH₂CH₂SO₃⁻) | 9 |
| K | −CH₂N⁺(pyridine-3-CO₂⁻) | 9 |

TABLE I-continued

| | | |
|---|---|---|
| (−) | −CH₂N⁺(imidazole-NCH₂CH₂OH) | 7 |
| (−) | −CH₂N⁺(pyridine-3-NH₂) | 9 |
| (−) | −CH₂N⁺(pyridine-2-NH₂-4-CH₂S(O)CH₃) | 9 |
| (−) | −CH₂N⁺(pyridine-4-CH₂OH) | 9 |
| (−) | −CH₂N⁺(pyridine-3-CH₂OH-5-NH₂) | 9 |
| (−) | −CH₂N⁺H(CH₃)₂ | 9 |
| (−) | −CO₂CH₂CH₂N⁺H(CH₃)₂ | 1 |
| (−) | −NSO₂CH₂CH₂N⁺(imidazole-N−CH₃)H | 1 |
| (−) | −OCH₂CH₂N⁺(pyridine-2-NH₂) | 9 |
| (−) | −SCH₂CH₂N⁺(pyridine-2-NH₂) | 1 |
| (−) | −SO₂CH₂CH₂N⁺(pyridine-2-NH₂) | 9 |
| (−) | −CH₂OCH₂CH₂N⁺(pyridine-2-NH₂) | 1 |

TABLE I-continued

| | Structure | |
|---|---|---|
| (−) | −CH₂SCH₂CH₂N⁺(pyridine-2-NH₂) | 1 |
| (−) | −CH₂S(O₂)CH₂N⁺(pyridine-2-NH₂) | 9 |
| (−) | −CH₂CH₂N⁺(pyridine-2-NH₂) | 9 |
| (−) | −C(O)CH₂N⁺(pyridine-2-NH₂) | 9 |
| (−) | −S(O₂)NHCH₂CH₂N⁺(pyridine-2-NH₂) | 9 |
| (−) | −S(→O)−CH₂N⁺(imidazole-N−CH₃) | 1 |
| (−) | −C(O)CH₂−N⁺(imidazole-N−CH₃) | 1 |
| (−) | −S(O₂)CH₂N⁺(imidazole-NMe) | 1 |
| (−) | −CH₂S(pyridine-N⁺-NH₂) | 9 |
| (−) | −CH=CH−(pyridinium-N−CH₃) | 9 |
| K | −CH₂NH(pyridine-2-yl) | 9 |
| (−) | −C(O)NHCH₂(1-methylpyridinium-2-yl) | 1 |
| (−) | −C(O)NHCH₂CH₂(1-methylpyridinium-4-yl) | 1 |
| (−) | −S(O₂)N(piperazinium with N,N-diCH₃) | 1 |
| (−) | −S(O₂)CH₂CH₂(1-methylpyridinium-2-yl) | 1 |
| (−) | −CH₂(1-methyl-2-amino-pyridinium-4-yl) | 9 |
| (−) | −CH₂(1-(CH₂C(O)NH₂)-pyridinium-4-yl) | 9 |
| K | −C(O)NHCH₂CH₂(pyridinium-N-oxide-2-yl) | 1 |
| K | −S(O₂)CH₂(pyridinium-N-oxide-4-yl) | 1 |
| (−) | −C(O)NH(1-methylpiperidinium-4-yl) | 1 |
| (−) | pyrrolidinium-N⁺-CH₃ | 9 |
| (−) | −CH₂(N⁺(CH₃)-morpholine) | 10 |
| (−) | −CH₂−N⁺(CH₃)₃ | 9 |

TABLE I-continued

| M | $R^a$ | $R^a$ Position | $R^{a'}$ | $R^{a'}$ Position |
|---|---|---|---|---|
| (−) | | | −CH₂−N⁺(piperidine) | 9 |
| K | | | −CH₂−N⁺(piperidine-CO₂⁻) | 9 |
| K | | | −CH₂−N⁺(morpholine with O⁻) | 7 |
| (−) | | | −CH₂−N⁺(piperazine N-oxide) | 10 |
| (−) | | | −C(O)NH−CH₂−(N⁺(CH₃)₂ piperidine) | 1 |
| (−) | CN | 1 | −CH₂N⁺(imidazole-NCH₃) | 9 |
| (−) | SOCH₃ | 1 | −CH₂N⁺(imidazole-NCH₃) | 9 |
| (−) | CO₂K | 1 | −CH₂N⁺(imidazole-NCH₃) | 9 |
| (−) | CO₂K | 1 | −CH₂N⁺(pyridine-NH₂) | 9 |
| (−) | tetrazole-NK | 1 | −CH₂N⁺(pyridine-NH₂) | 7 |
| (−) | tetrazole-NK | 1 | −CH₂N⁺(pyridine-NH₂) (para) | 9 |
| (−) | SO₃K | 1 | −CH₂N⁺(pyridine-NH₂) (para) | 9 |
| (−) | CO₂K | 1 | −N⁺(CH₃)(pyrrolidine) | 10 |
| (−) | SO₃K | 1 | −CH₂−N⁺(CH₃)(pyrrolidine) | 7 |
| (−) | SO₃K | 7 | −CH₂−N⁺(CH₃)(pyrrolidine) | 9 |
| (−) | CHO | 1 | −CH₂N⁺(pyridine-NH₂) | 9 |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lacetate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, trichloroethyl, silyl such as trimethylsilyl, trimethylsilylethyl, phenacyl, p-methoxybenzyl, acetonyl, o-nitrobenzyl, p-methoxyphenyl, 4-pyridylmethyl, and t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed July 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications (1) define the procedure for determining DHP susceptibility of the present carbapenems and (2) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

EXAMPLE 1

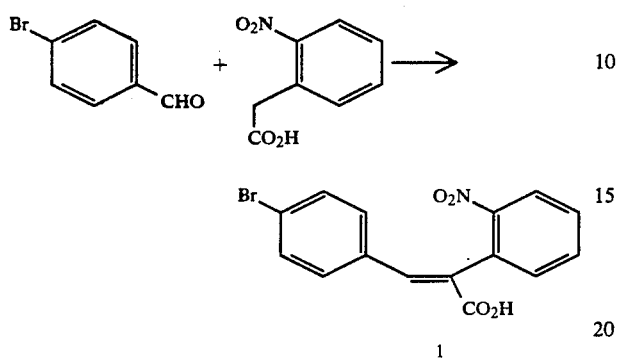

a-(2-nitrophenyl)-p-bromocinnamic acid (1)

A solution of 4-bromobenzaldehyde (27.75 g, 0.150 mol), 2-nitrophenylacetic acid (27.18 g, 0.150 mol) and triethylamine (21.0 ml, 0.150 mol) in 150 ml of acetic anhydride was heated at 40° C. for 38 hours and then poured into 900 ml of water and stirred until the organic layer solidified. The solid was isolated by filtration and dried in vacuo to yield 48.3 g (92%) of the title compound as a tan solid which was sufficiently pure to use directly in the next reaction.

$^1$H-NMR (300 MHz,d$_6$-acetone): d 7.06 (d,J=8.6Hz,2H), 7.25 (m,1H), 7.39 (d,J=8.6Hz,2H), 7.65 (m,2H), 7.87(s,1H,HC=C), 8.2 (m,1H).

EXAMPLE 2

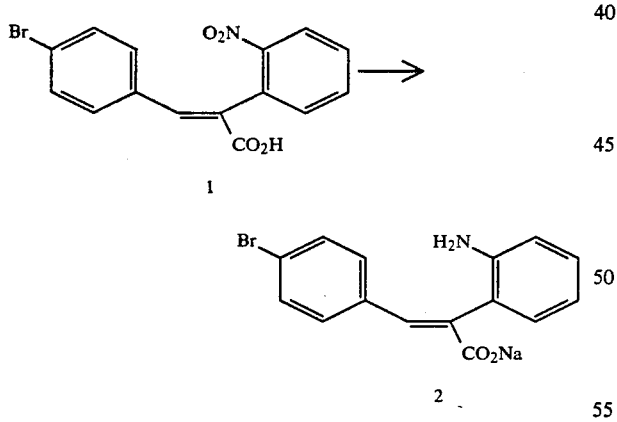

Sodium a-(o-aminophenyl)-p-bromocinnamate (2)

To a mixture of FeSO$_4$.7H$_2$O (163 g, 0.586 mol) in 180 ml of water was added 720 ml of 2.5N NaOH and the mixture was stirred and heated at 80° C. A solution of cinnamic acid derivative 1 (20.40 g, 0.05859 mol) in 180 ml of 0.5N NaOH was added dropwise. After the addition was complete, the temperature was increased to 100° C. and maintained for 30 min. The mixture was filtered while hot, and the filtrate was allowed to cool gradually to room temperature. The resulting solid was isolated by filtration to yield, after drying in vacuo, 12.1 g (61%) of the title compound as a tan solid which was used in the next reaction without purification.

$^1$H-NMR (300 MHz, 2:1 D$_2$O/CD$_3$CN): d 6.95–7.15 (m,3H), 7.18 (d,J=7.3Hz,2H), 7.39 (t, J=7.6Hz, 1H), 7.53 (d, J=7.3Hz, 2H), 7.72 (s, CH=C, 1H).

EXAMPLE 3

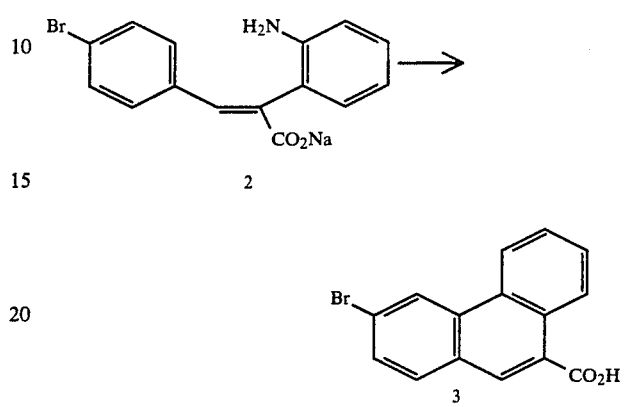

3-Bromophenanthrene-9-carboxylic acid (3)

A suspension of the amino-carboxylate 2 (13.3 g, 39.1 mmol) in 155 ml of ethanol was cooled to 0° C. and isoamyl nitrite (18.0 ml, 134 mmol) was added followed by dropwise addition of 15% ethanolic HCl (125 ml) during 1 hour. The resulting brown slurry was stirred at 0° C. for 2 hours more, and was then added gradually to a vigorously stirred suspension of copper powder (1.8 g) in a solution of NaH$_2$PO$_2$.H$_2$O (41.4 g, 391 mmol) and conc. H$_2$SO$_4$ (3 drops) in 63 ml of water which was maintained at 40° C. After the addition was complete, the mixture was stirred at 40° C. for 1 hour and was then cooled to 0° C. and the solid was isolated by filtration, washing with water. Drying in vacuo gave 9.9 g of a brown solid which was taken-up in CH$_2$Cl$_2$-THF, filtered to remove some inorganic material, and evaporated to yield 7.28 g (62%) of the title compound as a tan solid. This compound was used in the next reaction without purification.

$^1$H-NMR (300 MHZ, d$_6$-acetone): d 7.75 (m, 2H), 7.82 (dd, J=8.5, 1.8 Hz, 1H), 8.07 (d, J=8.5 Hz, 1H), 8.58 (s, 1H), 8.84 (m, 1H), 9.00 (s, 1H), 9.01 (m, 1H).

EXAMPLE 4

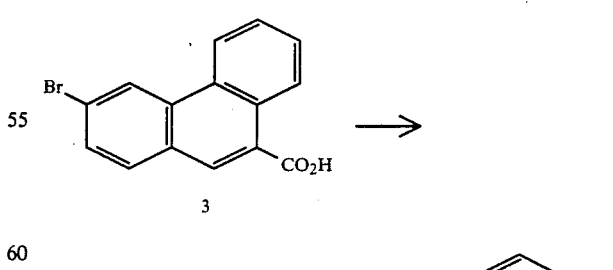

3-Bromo-9-(hydroxymethyl)-phenanthrene (4)

A solution of 3-bromo-phenanthrene-9-carboxylic acid (6.27 g, 20.8 mmol) in 100 ml of THF was cooled to 0° C. and a solution of borane in THF (1.0M, 25 ml, 25 mmol) was added dropwise. The cooling bath was removed, and the solution was stirred at room temperature for 19 hours and was then quenched by the cautious addition of methanol (25 ml). The solution was evaporated to dryness in vacuo and the residue was dissolved in methanol —CH$_2$Cl$_2$ (1:1) and again evaporated. After one repetition of this dissolution-evaporation process, 5.96 g (100%) of the title compound was obtained as a brown solid which was used in the next reaction without purification.

$^1$H-NMR (300 MHz, CDCl$_3$): d 5.17 (s, 2H), 7.6–7.8 (m, 5H), 8.12 (m, 1H), 8.61 (m, 1H), 8.76 (s, 1H).

EXAMPLE 5

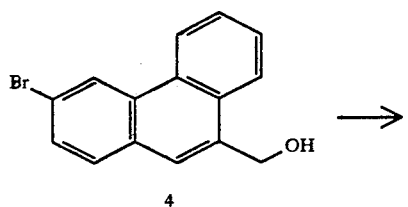

3-Bromo-9-(t-butyldimethylsilyloxymethyl)-phenanthrene (5)

To a solution of 3-bromo-9-(hydroxymethyl)-phenanthrene, 4 (5.96 g, 20.8 mmol) and t-butyldimethylsilyl chloride (4.7 g, 31 mmol) in 100 ml of CH$_2$Cl$_2$ and 20 ml of THF was added triethylamine (4.9 ml, 35 mmol) followed by 4-dimethylaminopyridine (250 mg, 2.05 mmol). After stirring at room temperature for 20 hours, the solution was poured into 300 ml of ethyl ether and washed successively with sat. NH$_4$Cl, sat. NaHCO$_3$, H$_2$O, and brine. Drying (Na$_2$SO$_4$) and evaporation gave a brown solid which was purified by flash chromatography through 400 g of silica gel (1:4 CH$_2$Cl$_2$-hexane) to yield 7.23 g (87%) of the title compound as a pale yellow solid.

$^1$H-NMR (300 MHz, CDCl$_3$): d 0.172 (s, 6H), 0.995 (s, 9H), 5.21 (s, 2H), 7.66 (m, 3H), 7.76 (d, J=8.5Hz, 1H), 7.81 (s, 1H), 8.01 (m, 1H), 8.62 (m, 1H), 8.79 (d, J=1.71 Hz, 1H).

FAB-MS: m/e=400,402 (M+).

EXAMPLE 5A

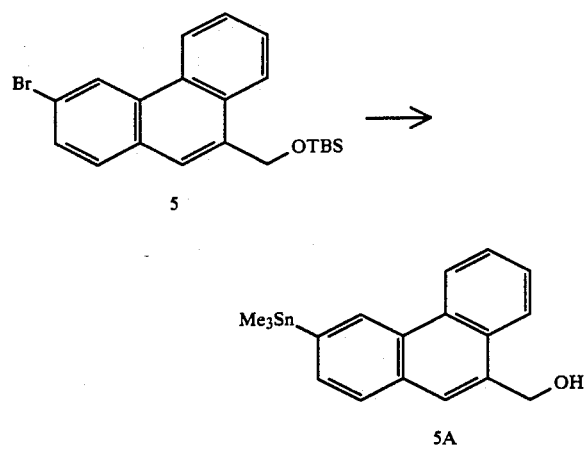

3-Trimethylstannyl-9-(hydroxymethyl)-phenanthrene (5A)

Bromophenanthrene 5 (1.02 g, 2.5 mmol) was dissolved in anhydrous THF (15 mL) and cooled to −78° C. under nitrogen. To this stirred solution was added a solution of t-Butyllithium in pentane (2.2 equiv.; 5.5 mmol; 3.0 mL). After 30 minutes at −78° C., the reaction was warmed to −50° C. for 20 minutes, after which time Me$_3$SnCl (1.1 equiv.; 2.75 mmol; 548 mg) was added as a solid. The cold bath was removed and the reaction allowed to reach ambient temperature. After 75 minutes, the reaction was quenched with water. The solvent was removed in vacuo and the residual dissolved in Et$_2$O. Washing with water and brine was followed by drying over MgSO$_4$, filtering and removal of solvent. The residual was dissolved in anhydrous THF and treated with a 1.0M solution of n-Bu$_4$NF in THF (1.1 equiv.; 2.75 mmol; 2.75 mL) at ambient temperature for 5 minutes. Quenching the reaction with saturated NH$_4$Cl was followed by removal of the solvent in vacuo. The residual was dissolved in EtOAc and washed with water and brine, dried (MgSO$_4$), filtered and the solvent removed in vacuo. Purification by flash chromatography (25% EtOAc/hexanes) provided 733 mg (78%) of stannyl alcohol 5A as a white solid.

$^1$H-NMR (300 MHz, CDCl$_3$): d 0.43 (s, 9H), 2.05 (broad s, 1H), 5.11 (s, 2H), 7.58–7.71 (m, 4H), 7.79 (d, J=7.7 Hz, 1H), 8.08 (d, J=7.7 Hz, 1H), 8.70–8.89 (m, 2H).

EXAMPLE 6

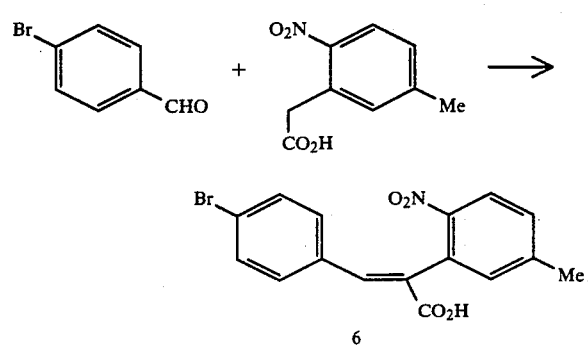

a-(2-nitro-5-methyl-phenyl)-p-bromocinnamic acid (6)

To a mixture of 4-bromobenzaldehyde (19.5 g, 106 mmol) and 2-nitro-5-methyl-phenylacetic acid (20.6 g, 106 mmol; J. G. Atkinson et. al., *Tetrahedron Lett.*, 2857, 1979) in 100 ml of acetic anhydride was added triethylamine (14.7 ml, 106 mmol) and the resulting reddish solution was heated at 40° C. for 70 hours. Most of the acetic anhydride was evaporated under vacuum and the residue was diluted with ethyl acetate and washed with sat. NH$_4$Cl, H$_2$O, and brine. Drying (MgSO$_4$) and evaporation yielded 37.87 g (99%) of product as a yellow solid which was used in the next reaction without purification.

$^1$H-NMR (300 MHz, d$_6$-acetone): d 2.31 (s, 3H), 7.06 (d, J=8.6 Hz, 2H), 7.08 (s, 1H), 7.39 (d, J=8.6 Hz, 2H), 7.44 (d, J=8.40 Hz, 1H), 7.83 (s, 1H), 8.13 (d, J=8.4 Hz, 1H).

EXAMPLE 7

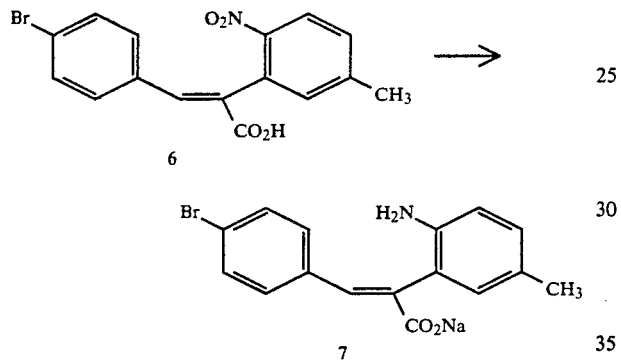

Sodium a-(2-amino-5-methyl-phenyl)-p-bromocinnamate (7)

Following the procedure described in Example 2, the nitrophenylcinnamic acid derivative 6 (39.60 g, 110.0 mmol) was reduced with FeSO$_4$—NaOH to yield 36.46 g (93%) of amino-carboxylate 7 as a yellow powder which was used in the next reaction without purification.

$^1$H-NMR (200 MHz, 2:1 D$_2$O/CD$_3$CN): d 2.47 (s, 3H), 7.03 (bs, 1H), 7.05 (d, J=9Hz, 1H), 7.32 (d, J=9Hz, 3H), 7.64 (d, J=9Hz, 2H), 7.82 (s, 1H).

EXAMPLE 8

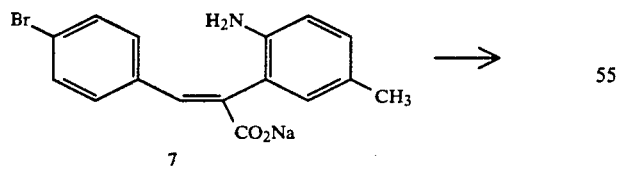

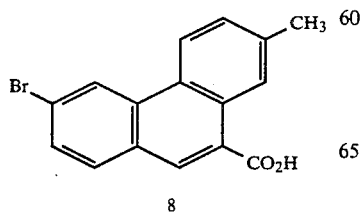

3-Bromo-7-methyl-phenanthrene-9-carboxylic acid (8)

The amino-carboxylate 7 (36.3 g, 102 mmol) was cyclized following the procedure described in Example 3 to yield 28.48 g (89%) of crude product as a brown solid. This material was extremely insoluble and was thoroughly extracted with CH$_2$Cl$_2$-THF-acetone and filtered. The filtrate was evaporated to leave 5.93 g of a brown solid. This "more soluble" portion of the crude material was utilized in the following example.

$^1$H-NMR (300 MHz, d$_6$-acetone): d 2.59 (s, 3H), 7 63 (d, J=8.6 Hz, 1H), 7.82 (dd, J=8.55, 1.7 Hz, 1H), 8.07 (d, J=8.55 Hz, 1H), 8.59 (s, 1H), 8.80 (d, J=8.6 Hz, 1H), 8.99 (d, J=1.7 Hz, 1H).

FAB-MS: M/e=314,316 (M+).

EXAMPLE 9

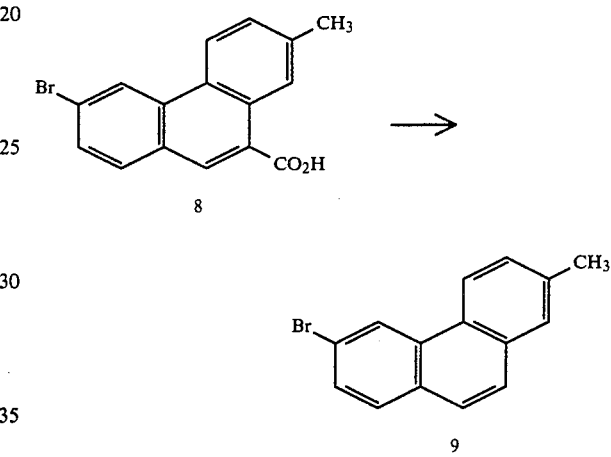

3-Bromo-7-methyl-phenanthrene (9)

A stirred mixture of 3-Bromo-7-methyl-phenanthrene-9-carboxylic acid (5.50 g, 17.5 mmol) and CuCO$_3$.-Cu(OH)$_2$.H$_2$O (1.5 g) in 50 ml of quinoline was rapidly heated to 210° C. Gas evolution was observed and the mixture became extremely dark. After 10 min the mixture was allowed to cool to room temperature and was diluted with PhCH$_3$—CH$_2$Cl$_2$ (9:1) and filtered. The filtrate was washed with 1N HCl (2x) and brine. Drying (Na$_2$SO$_4$) and evaporation gave 4.89 g of a brown oil which was flash chromatographed through 450 g of silica gel (10% CH$_2$Cl$_2$/hexane) to yield 2.63 g (56%) of the title compound as a pale yellow solid.

$^1$H-NMR (300 MHz, CDCl$_3$): d 7.46 (dd, J=8.4, 1.5Hz, 1H), 7.6–7.7 (m, 4H), 7.70 (d, J=8.52Hz, 1H), 8.43 (d, J=8.52 Hz, 1H), 8.74 (d, J=1.5Hz, 1H).

FAB-MS: m/e=270,272 (M+).

EXAMPLE 10

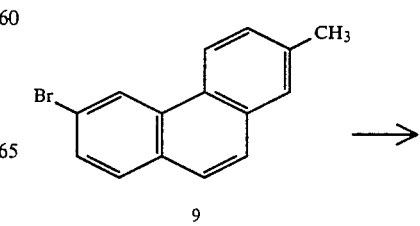

-continued

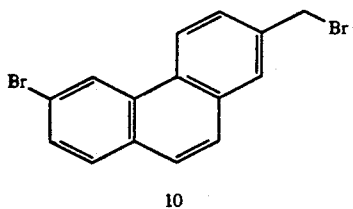

3-Bromo-7-(bromomethyl)-phenanthrene (10)

A mixture of 3-bromo-7-methylphenanthrene (2.640 g, 9.736 mmol) and N-bromosuccinimide (1.733 g, 9.736 mmol) in 200 ml of carbon tetrachloride was heated to reflux and benzoyl peroxide (25 mg) was added. After 2.5 hour a starch-iodide test showed that no NBS remained and the mixture was cooled to room temperature, washed with water, dried (MgSO$_4$) and evaporated to give 3.14 g of crude product as a solid. Flash chromatography through 330 g of silica gel (10% CH$_2$Cl$_2$/hexane) gave 2.719 g of a white solid which was recrystallized from 70 ml of cyclohexane (reflux to RT) to yield 2.061 g (60%) of the title compound as a white solid, mp 147°–148° C.

$^1$H-NMR (300MHz, CDCl$_3$): d 7.64–7.74 (m, 5H), 7.87 (d, J=1.87 Hz, 1H), 8.54 (d, J=8.58, 1H), 8.75 (d, J=1.43, 1H).

FAB-MS: m/e=348,350,352 (M+)

EXAMPLE 11

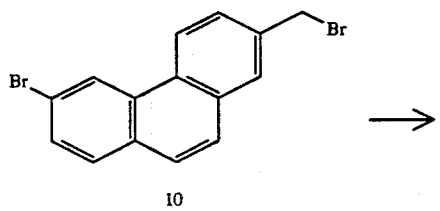

3-Bromo-7-(acetoxymethyl)-phenanthrene (11)

A mixture of 3-bromo-7-(bromomethyl)-phenanthrene (2.249 g, 6.425 mmol) and potassium acetate (1.26 g, 12.8 mmol) in 60 ml of DMF was heated at 80° C. for 7 hours. After cooling to TR, the reaction mixture was diluted with ethyl ether, washed with water and brine, dried (MgSO$_4$) and evaporated to give 2.042 g (97%) of the title compound as a white solid which was used in the following reaction without purification.

$^1$H-NMR (300 MHz, CDCl$_3$): d 2.15 (s, 3H), 5.30 (s, 2H), 7.6–7.8 (m, 5H), 7.84 (bs, 1H), 8.54 (d, J=8.67Hz, 1H), 8.75 (d, J=1.7Hz, 1H).

EXAMPLE 12

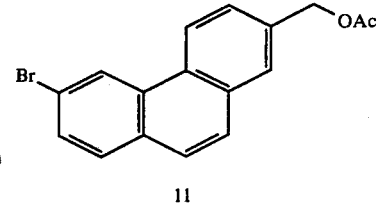

3-Bromo-7-(hydroxymethyl)-phenanthrene (12)

A solution of 3-bromo-7-(acetoxymethyl)-phenanthrene (2.042 g, 6.20 mmol) in 50 ml of THF was cooled to 0° C. and a solution of diisobutylaluminum hydride in hexane (1.0M, 14 ml, 14 mmol) was added dropwise. After 30 minutes, the solution was cautiously hydrolyzed with 1N HCl and was then diluted with ethyl acetate and washed successively with 1N HCl, sat. NaHCO$_3$, H$_2$O, and brine. Drying (MgSO$_4$) and evaporation gave 1.77 g (99%) of the title compound as a white solid which was used in the next reaction without purification.

$^1$H-NMR (300 MHz, CDCl$_3$): d 4.91 (s, 2H), 7.6–7.8 (m, 5H), 7.86 (s, 1H), 8.56 (d, J=8.67 Hz, 1H), 8.78 (s, 1H).

EXAMPLE 13

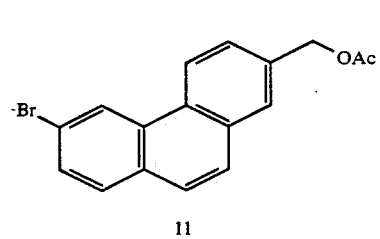

3-Bromo-7-(t-butyldimethylsilyloxymethyl)-phenanthrene (13)

Following the procedure described in Example 5, 3-bromo-7-(hydroxymethyl)-phenanthrene (1.886 g, 6.568 mmol) was silylated to yield 2.584 g (98%) of the title compound as a white solid.

¹H-NMR (300 MHz, CDCl₃): d 0.143 (s, 6H), 0.979 (s, 9H), 4.95 (s, 2H), 7.6–7.8 (m, 5H), 7.82 (bs, 1H), 8.54 (d, J=8.52Hz, 1H), 8.78 (d, J=1.65, 1H).

FAB-MS: m/e=400,402 (M+).

EXAMPLE 14

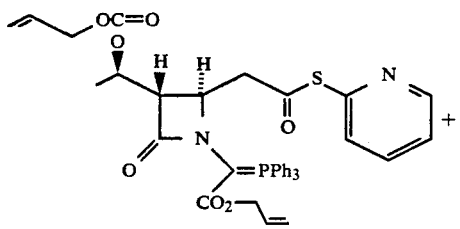

14

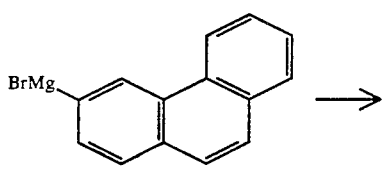

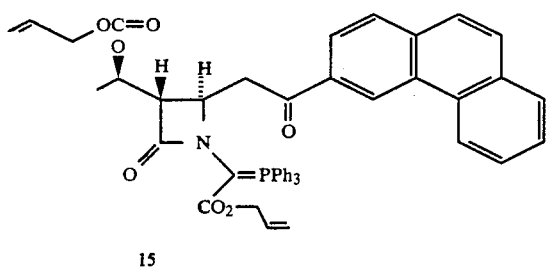

15

(3S,4R)-1-(allyloxycarbonyltriphenylphosphoranylidene)methyl-3-[1R-(allyloxycarbonyloxy)ethyl]-4-(3-phenanthrenyl-carbonyl)methylazetidin-2-one (15)

To a mixture of 3-bromophenanthrene (155.7 mg, 0.606 mmol) and magnesium turnings (22 mg, 0.91 mmol) in 2 ml of THF was added 1,2-dibromoethane (0.010 ml) and the reaction mixture was sonicated briefly in an ultrasonic bath to initiate the Grignard formation and was then heated at 50° C. for 2.25 hours.

The above Grignard solution was added dropwise to a solution of 0.350 g (0.500 mmol) of (3S,4R)-1-(allyloxycarbonyltriphenylphosphoranylidene)methyl-3-[1R-(allyloxycarbonyloxy)ethyl]-4-(2-pyridylthio)carbonyl)methyl-azetidin-2-one, 14, in 2.5 ml of THF at 0° C. After 1 hour, the reaction mixture was hydrolyzed with sat. NH₄Cl solution, diluted with a large volume of ethyl ether, and washed successively with sat. NH₄Cl, 1N NaOH (2x), H₂O, and brine. Drying (MgSO₄) and evaporation gave a yellow oil which was purified by flash chromatography through 40 g of silica gel (7:3 EtOAc/hexane) to yield 91.3 mg (24%) of the title compound as a yellow foam.

¹H-NMR (300 MHz, CDCl₃): inter alia; d 1.20 (d, J=6.23 Hz, 3H, CH₃).

IR (CHCl₃): 1745 (β-lactam), 1680 (ketone), 1615 cm⁻¹ (ylide).

EXAMPLE 15

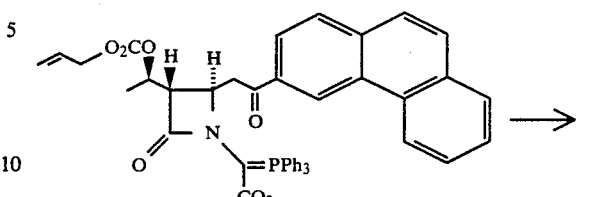

15

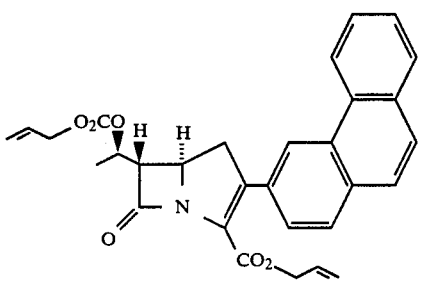

16

Allyl-(5R,6S)-2-(3-phenanthrenyl)-6-[1R-(allyloxycarbonyloxy)ethyl]-carbapen-2-em-3-carboxylate(16)

A solution of the phosphorane 15 (91.0 mg, 0.117 mmol) and a crystal of hydroquinone in 10 ml of p-xylene was heated to reflux (138° C.). After 1 hour, the solution was cooled to room temperature, concentrated under high vaccum, and the residual oil was purified by flash chromatography through 10 g of silica gel (35% EtOAc/hexane) to yield 51.5 mg (88%) of the title compound as a pale yellow oil.

¹H-NMR(300 MHz, CDCl₃): d 1.53 (d, J=6.35 Hz, 3H, CH₃), 3.33–3.55 (m, 3H, H1, H6), 4.38 (ddd, J=2.8, 9.2, 9.4 Hz, 1H, H5), 4.6–4.8 (m, 4H, —OCH₂C≡C) 5.08–5.44 (m, 5H, —C≡CH₂, H8), 5.75–6.05 (m, 2H, —CH≡C), 7.55–7.95 (m, 7H, ArH), 8.62 (d, J=8.1 Hz, 1H, ArH), 8.73 (s, 1H, ArH).

IR (CHCl₃): 1780 (β-lactam), 1745 (carbamate), 1725 cm⁻¹ (ester).

UV (CH₃CN): 1max=237 nm (e=17,000), 251 (e=47,000).

EXAMPLE 16

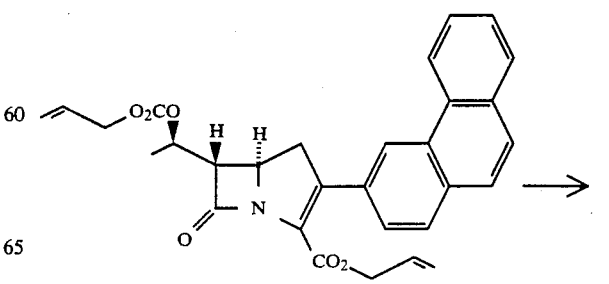

16

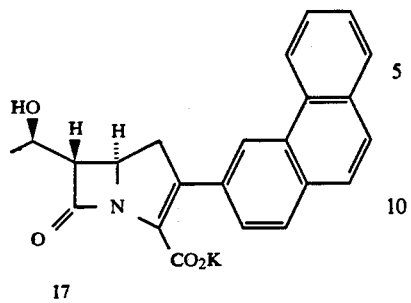

17

Potassium (5R,6S)-2-(3-phenanthrenyl)-6-(1R-hydroxyethyl)-carbapen-2-em-3-carboxylate (17)

To a solution of the carbapenem 16 (51.0 mg, 0.103 mmol) in 0.6 ml of ethyl acetate at 0° C. were added in sequence a solution of potassium 2-ethylhexanoate in ethyl acetate (0.50M, 0.206 ml), a solution of 2-ethylhexanoic acid in methylene chloride (1.0M, 0.103 ml), triphenylphosphine (8.0 mg, 0.031 mmol) and tetrakis(triphenylphosphine)palladium (12 mg, 0.010 mmol). The reaction mixture was stirred at 0° C. for 1 hour, and was then pipetted into a centrifuge tube containing cold ethyl ether (2ml). The precipitate was isolated by centrifugation, washing twice with ethyl ether. Purification by reverse-phase preparative TLC (2:1 $H_2O/CH_3CN$) yielded 23.0 mg (54%) of the title compound as an off-white lyophilized solid.

$^1$H-NMR (300 MHz, 2:1 $D_2O/CD_3CN$): d 1.66 (d, J=6.41 Hz, 3H, $CH_3$), 3.59 (dd, J=9.8, 16.7 Hz, 1H, H1a), 3.83 (dd, J=2.7, 6.0 Hz, 1H, H6), 3.96 (dd, J=8.6, 16.7 Hz, 1H, H1b), 4.54–4.64 (m, 1H, H8), 4.69 (ddd, J=9.9, 9.2, 2.7 Hz, 1H, H5), 7.96–8.14 (m, 3H, ArH), 8.16 (s, 2H, ArH), 8.26 (d, J=8.4 Hz, 1H, ArH), 8.33 (dd, J=1.4, 7.7 Hz, 1H, ArH), 9.07 (s, 1H, ArH), 9.10 (d, J=7.7 Hz, 1H, ArH).

IR (KBr): 1750 ($\beta$-lactam), 1600 cm$^{-1}$ (carboxylate).

UV ($H_2O$): 1max=325 nm (e=16,400).

EXAMPLE 17

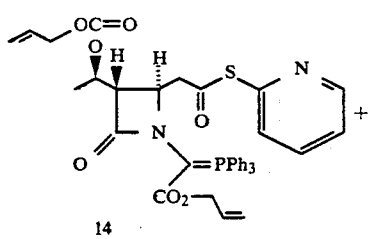

14

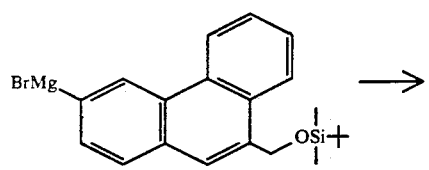

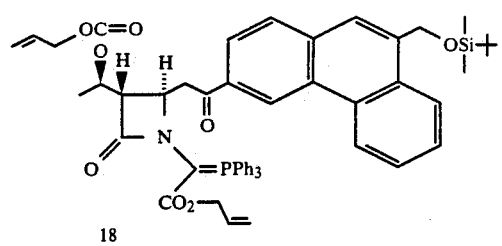

18

(3S,4R)-1-(allyloxycarbonyltriphenylphosphoranylidene)methyl-3-[1R-(allyloxycarbonyloxy)ethyl]-4-[9-(t-butyldimethyl-silyloxymethyl)-3-phenanthrenylcarbonyl]methyl-azetidin-2-one (18)

A solution of 3-bromo-9-(t-butyldimethylsilyloxymethyl)-phenanthrene 5 (1.781 g, 4.437 mmol) in 20 ml of THF was cooled to −70° C. and a solution of t-butyllithium in pentane (1.7M, 5.35 ml, 9.1 mmol) was added dropwise. The initial yellow solution became a light-green suspension as the temperature was allowed to warm to −10° C. Upon addition of a freshly prepared solution of magnesium bromide in THF (0.25M, 20 ml, 5.0 mmol) a bright yellow solution was obtained which was re-cooled to −70° C. and cannulated gradually into solution of (3S,4R)-1-(allyloxycarbonyltriphenylphosphoranylidene)methyl-3-[1R-(allyloxycarbonyloxy)ethyl]-4-[(2-pyridylthio)carbonyl]methyl-azetidin-2-one (14) (3.145 g, 4.437 mmol) in 25 ml of THF at −70° C. The reaction mixture was allowed to warm gradually to −20° C. during 45 minutes and was then hydrolyzed with sat. $NH_4Cl$ and diluted with a large volume of ethyl ether. The organic layer was washed successively with sat. $NH_4Cl$, 1N NaOH (2x), $H_2O$, and brine. Drying ($MgSO_4$) and evaporation gave an oil which was purified by flash chromatography through 400 g of silica gel (1:1 EtOAc/hexane) to yield 2.869 g (70%) of the title ketone as a pale yellow foam.

$^1$H-NMR (300 MHz, $CDCl_3$); inter alia; d 0.185 (s, 6H, SiMe$_2$), 1.00 (s, 9H, Sit-Bu), 1.18 (d, J=6.3 Hz, 3H, CH$\underline{CH_3}$), 5.26 (s, 2H, —CH$_2$OSi).

IR (CHCl$_3$): 1745 ($\beta$-lactam), 1680 (ketone), 1615 cm$^{-1}$ (ylide).

FAB-MS: m/e=920 (M+H)

EXAMPLE 18

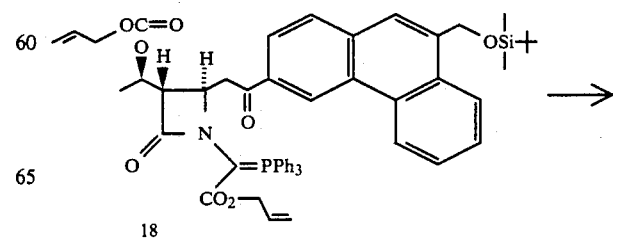

18

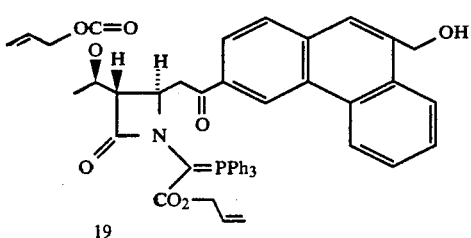

19

(3S,4R)-1-(allyloxycarbonyltriphenylphos-
phoranylidene)methyl-3-[1R-(allyloxycarbonyloxy)e-
thyl]-4-[9-(hydroxymethyl)-3-phenanthrenylcarbonyl]-
methyl-azetidin-2-one (19)

A solution of the silyl ether 18 (3.092 g, 3.360 mmol) in 30 ml of methanol was cooled to 0° C. and a solution of methanolic sulfuric acid (1.0M, 5.5 ml) was added. After 2.5 hours, the solution was basified with sat. NaHCO$_3$, and then diluted with a large volume of ethyl acetate and washed successively with sat. NaHCO$_3$, H$_2$O (2x), and brine. Drying (MgSO$_4$) and evaporation gave an oil which was purified by flash chromatography through 300 g of silica gel (EtOAc) to yield 2.81 g (100%) of the title compound as a yellow foam.

$^1$H-NMR (300 MHz, CDCl$_3$): inter alia; d 1.19 (d, J=6.16 Hz, 3H, CHC$\underline{H}_3$), 5.05 (s, 2H, ArC$\underline{H}_2$O).

IR (CHCl$_3$): 3300–3600 (OH), 1745 (β-lactam), 1680 (ketone), 1615 cm$^{-1}$ (ylide).

FAB-MS: m/e=806 (M+H).

EXAMPLE 19

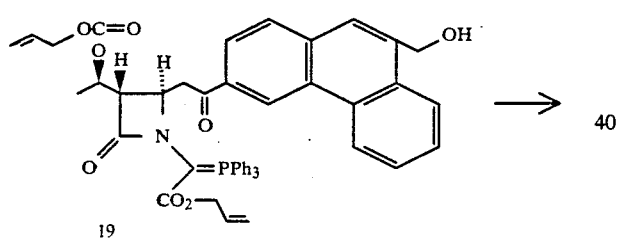

Allyl-(5R,6S)-2-(9-hydroxymethyl-3-phenanthrenyl)-6-
[1R-(allyoxycarbonyloxy)ethyl]-carbapen-2-em-3-car-
boxylate (20)

A solution of the phosphorane 19 (1.488 g, 1.846 mmol) and several crystals of p-hydroquinone in 60 ml of p-xylene was heated to reflux (138° C.). After 1.5 hour, the solution was cooled to room temperature, concentrated under high vacuum, and the residual oil was purified by flash chromatography through 150 g of silica gel (3:2 EtOAc/hexane) to yield 0.906 g (93%) of the title carbapenem as a yellow foam.

$^1$H-NMR (300 MHz, CDCl$_3$): d 1.46 (d, J=6.41 Hz, 3H, CH$_3$), 3.2–3.4 (m, 2H, H1), 3.39 (dd, J=8.2, 2.8 Hz, 1H, H6), 4.26 (dt, J=2.8, 8.9 Hz, 1H, H5), 4.55–4.75 (m, 4H, —OCH$_2$C=C), 5.08 (s, 2H, ArCH$_2$O—), 5.1–5.4 (m, 5H, —C=CH$_2$, CHC$\underline{H}_3$), 5.7–6.0 (m, 2H, —CH=C), 7.4–8.6 (m, 8H, ArH).

IR (CHCl$_3$): 3300–3600 (OH), 1780 (β-lactam), 1745 (carbonate), 1725 cm$^{-1}$ (ester).

UV (CH$_3$CN): 1max=328 nm (e=15,600), 252 (e=46,000).

FAB-MS: m/e=528 (M+H).

EXAMPLE 20

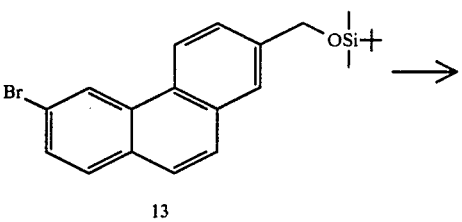

13

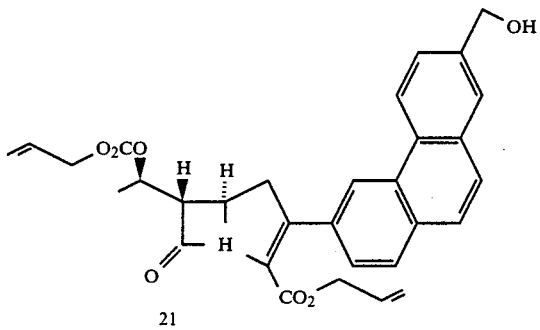

21

Allyl-(5R,6S)-2-(7-hydroxymethyl-3-phenanthrenyl)-6-
[1R-(allyloxycarbonyloxy)ethyl]-carbapen-2-em-3-car-
boxylate (21)

In an analogous manner to that described in Examples 17–19, but starting with the bromophenanthrene 13, the carbapenem 21 was obtained as a yellow oil.

$^1$H-NMR(300 MHz, CDCl$_3$): δ 1.50 (d, J=6.29 Hz, 3H, CH$_3$), 3.28–3.50 (m, 3H, H1, H6), 4.33 (ddd, J=2.8, 9.0, 9.7 Hz, 1H, H5), 4.58–4.76 (m, 4H, —OCH$_2$C=C), 4.88 (bs, 2H, ArCH$_2$O—), 5.06–5.42 (m, 5H, H8, —C=CH$_2$), 5.75–6.00 (m, 2H, —CH=C), 7.54 (dd, J=1.6, 8.3 Hz, 1H), 7.62 (dd, J=1.7, 8.6 Hz, 1H), 7.66–7.76 (ABq, J$_{AB}$=8.9 Hz, Δν$_{AB}$=12.5 Hz, 2H), 7.82 (d, J=8.3 Hz, 1H), 7.83 (s, 1H), 8.56 (d, J=8.6 Hz, 1H), 8.66 (s, 1H).

IR (CHCl$_3$): 3600 (OH), 1780 (β-lactam), 1745 (carbonate), 1725 cm$^{-1}$ (ester).

UV (CH$_3$CN): λmax=328 nm (ε=15,00), 253 nm (ε=47,000).

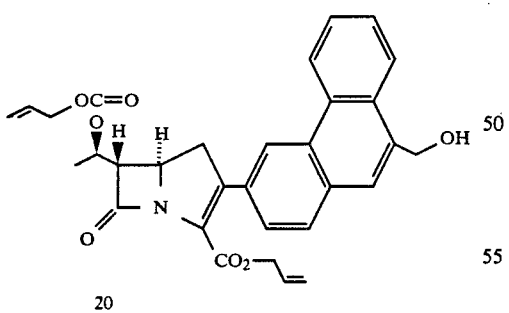

20

EXAMPLE 21

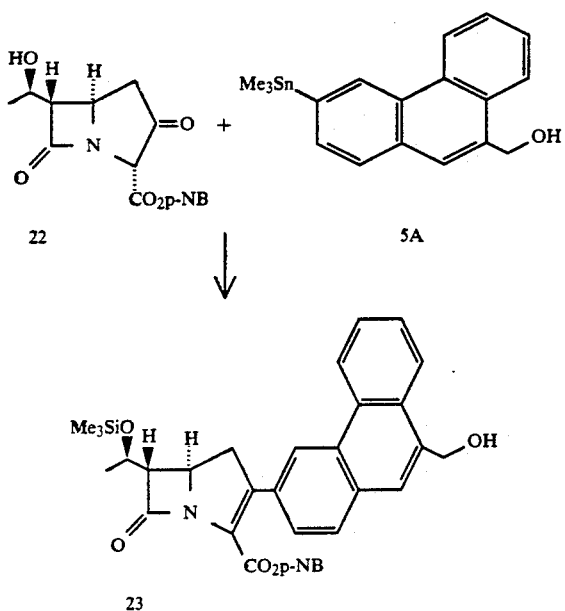

p-Nitrobenzyl-(5R,6S)-2-(9-hydroxymethyl-3-phenanthrenylo-6-[1R-(trimethylsilyloxy)ethyl]-carbapen-2-em-3-carboxylate (23)

A dry 15 mL receiving flask was charged with the bicyclic β-ketoester 22 (143 mg; 0.41 mmol) and a magnetic stir bar and the system was purged with nitrogen. Two mL of anhydrous tetrahydrofuran (THF) was added and upon dissolution of 22, the reaction vessel was cooled to −78° C. under N₂. Diisopropylamine (0.063 mL, 0.45 mmol) was then added and the stirring was continued for 10 minutes. Trifluoromethanesulfonic anhydride (0.075 mL, 0.45 mmol) was added, followed by stirring for an additional 15 mins. Triethylamine (0.062 mL, 0.45 mmol) was then added, followed by trimethylsilyltrifluoromethanesulfonate (0.087 mL, 0.45 mmol).

While the above reaction was stirred for 20 mins., the organostannane 5A (168 mg, 0.45 mmol), tris(dibenzylideneacetone)dipalladium-chloroform (8.5 mg, 0.0082 mmol) and tris(2,4,6-trimethoxyphenyl)-phospine (17.4 mg, 0.033 mmol) were weighed into a single vial and the vial was purged with nitrogen. When the above reaction time had elapsed, N-methylpyrrolidinone (2 mL) was added to the initial reaction mixture followed by the previously weighed solids. A 0.87M zinc chloride in ether solution (0.52 mL, 0.45 mmol) was then added. The low temperature bath was then removed and the reaction vessel was placed in a luke warm water bath to allow it to quickly reach ambient temperature. After reaching ambient temperature, the mixture was stirred for 13 minutes. The reaction was then quenched by pouring the contents of the flask into a 125 mL separatory funnel containing diethyl ether, ethyl acetate and water. The organic phase was separated and washed with water and brine. The organic phase was dried over magnesium sulfate. The mixture was then filtered and the solvent removed under vacuum. Flash column chromatography of the residue (silica gel, 40% ethyl acetate/hexanes) provided 169 mg (68%) of the desired carbapenem 23.

¹H-NMR (300 MHz, CDCl₃): δ 0.16 (s, 9H), 1.31 (d, J=6.1 Hz, 3H), 2.13 (broad s, 1H), 3.29 (dd, J=6.6, 2.0 Hz, 1H), 3.33-3.48 (m, 2H), 4.21-4.38 (complex m, 2H), 5.15 (AB$_q$, J$_{AB}$=13.6, Δν$_{AB}$=53.7 Hz, 2H), 5.17 (s, 2H), 7.08 (d, J=8.6 Hz, 2H), 7.45 (dd, J=8.2, 1.6 Hz, 1H), 7.56-7.77 (complex m, 6H), 8.05-8.10 (m, 1H), 8.43-8.47 (m, 1H), 8.52 (s, 1H).

IR (CHCl₃): 3600(w), 3520-3350(w), 1770(s), 1720(s), 1600(m), 1515(s) cm⁻¹.

UV (CH₃CN): λmax=252 nm, ε=25,200.

EXAMPLE 22

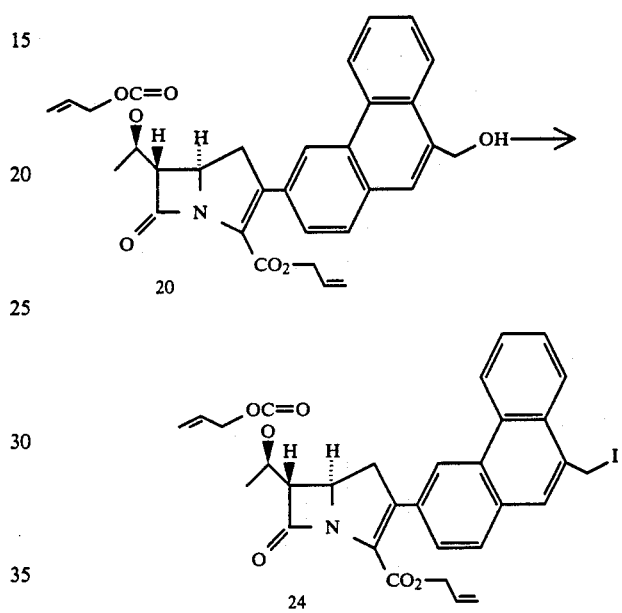

Allyl-(5R,6S)-2-(9-idomethyl-3-phenanthrenyl)-6-[1R-(allyoxycarbonyloxy)ethyl]-carbapen-2-em-3-carboxylate (24)

A solution of the carbapenem 20 (456.3 mg, 0.865 mmol) in 9 ml of methylene chloride was cooled to −40° C. and triethylamine (0.190 ml, 1.36 mmol) was added followed by dropwise addition of methanesulfonyl chloride (0.090 ml, 1.2 mmol). The reaction mixture was allowed to warm to −20° C. during 30 minutes and was then quenched with sat. NH₄Cl and diluted with ethyl acetate. The organic layer was washed with sat. NH₄Cl, sat. NaHCO₃, H₂O, and brine. Drying (MgSO₄) and evaporation gave a yellow oil which was dissolved in 8 ml of acetone, cooled to 0° C. in the dark, and anhydrous sodium iodide (0.260 g, 1.73 mmol) was added. After 5 minutes the ice-bath was removed and the mixture was stirred at room temperature for 1.5 h and then was diluted with ethyl acetate and washed successively with 5% Na₂S₂O₃, H₂O, and brine. Drying (MgSO₄) and evaporation yielded 563 mg (100%) of the title iodide as a yellow oil which was used directly in the next reaction without purification.

¹H-NMR (300 MHz, CDCl₃): δ 1.53 (d, J=6.5 Hz, 3H, CH₃), 3.3-3.5 (m, 2H, H1), 3.50 (dd, J=8.31, 2.75 Hz, 1H, H6), 4.37 (dt, J=2.75, 9.0 Hz, 1H, H5), 4.5-4.8 (m, 4H, —OCH₂C═C), 4.95 (s, 2H, —CH₂I), 5.1-5.4 (m, 5H, —C═CH₂, CHCH₃), 5.7-6.0 (m, 2H, —CH═C), 7.5-8.7 (m, 8H, ArH).

EXAMPLE 23

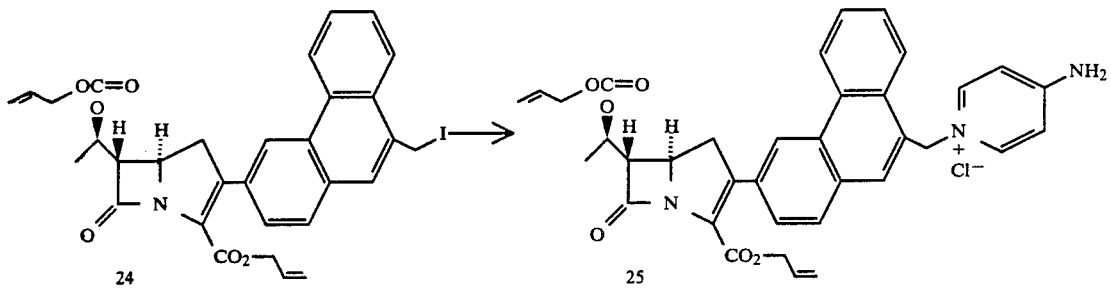

Allyl-(5R,6S)-2-[9-(4-aminopyridinium)methyl-3-phenanthrenyl]-6-[1R-(allyoxycarbonyloxy)ethyl]carbapen-2-em-3-carboxylate chloride (25)

A solution of the iodide 24 (563 mg, 0.865 mmol) in 8 ml of acetonitrile was cooled to 0° C. in the dark and 4-aminopyridine (90.0 mg, 0.956 mmol) was added. A precipitate began depositing almost immediately. After 1.5 hour, the mixture was diluted into a large volume of methylene chloride and washed successively with half-saturated NH$_4$Cl, H$_2$O, and brine. The solution retained some water due to the surfactant-like nature of the product and was thus diluted with toluene and evaporated to dryness in vacuo to azeotropically remove the water. The residue was extracted with methylene chloride and the extract was filtered through sodium sulfate and evaporated to yield 500 mg (90%) of the title compound as a yellow solid.

$^1$H-NMR (300 MHz, CDCl$_3$): δ 1.46 (d, J=6.1Hz, 3H, CH$_3$), 3.25-3.55 (m, 2H, H1), 3.52 (dd, J=7.8, 2.4 Hz, 1H, H6), 4.34 (dt, J=9.4Hz, 1H, H5), 4.5-4.7 (m, 4H, —OCH$_2$C=C), 5.0-5.4 (m, 5H, H8, —C=CH$_2$), 5.68 (bs, 2H, —CH$_2$N), 5.5-6.0 (m, 2H, —CH=C), 7.0-8.7 (m, 12H, ArH).

IR (CHCl$_3$): 1780 (β-lactam), 1740 (carbonate), 1725 (ester), 1660 cm$^{-1}$ (iminium).

EXAMPLE 24

(5R,6S)-2-[9-(4-aminopyridinium)methyl-3-phenanthrenyl]-6-(1R-hydroxyethyl)-carbapen-2-em-3-carboxylate (26)

To a solution of the carbapenem 25 (500 mg, 0.781 mmol) in 8 ml of methylene chloride and 4 ml of ethyl acetate at 0° C. were added in sequence a solution of potassium 2-ethylhexanoate in ethyl acetate (0.5M, 1.6 ml), a solution of 2-ethylhexanoic acid in methylene chloride (1.0M, 0.80 ml), and a solution of tetrakis(triphenylphosphine)palladium (90 mg, 0.078 mmol) and triphenylphosphine (60 mg, 0.23 mmol) in 5 ml of methylene chloride. After 2.5 hour the reaction mixture was pipetted into a centrifuge tube containing cold ethyl ether (20 ml). The solid was isolated by centrifugation, washing twice with cold ethyl ether. After drying under a stream of nitrogen and then in vacuo, 492 mg of a yellow solid was obtained. Purification by reverse-phase preparative TLC (elution with 2:1 H$_2$O/CH$_3$CN) yielded after lyophilization 88.0 mg (23%) of the title compound as a light yellow solid.

$^1$H-NMR (300 MHz, 2:1 D$_2$O/CD$_3$CN): δ 1.69 (d, J=6.47 Hz, 3H, CH$_3$), 3.55 (dd, J=9.9, 16.5 Hz, 1H, H1a), 3.85 (dd, J=6.0, 2.6 Hz, 1H, H6), 3.93 (dd, J=8.8, 16.5Hz, 1H, H1b), 4.55-4.75 (m, 2H, H5, H8), 6.07 (s, 2H, —CH$_2$N), 7.18 (d, J=7.0Hz, 2H), 7.94 (s, 1H) 8.0-8.3 (m, 5H), 8.39 (d, J=7.0Hz, 2H), 9.00 (s, 1H), 9.13 (d, J=8.2Hz, 1H).

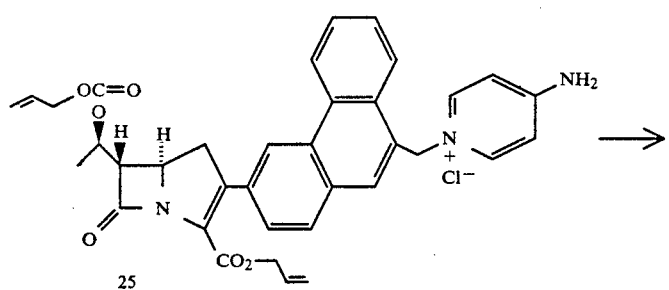

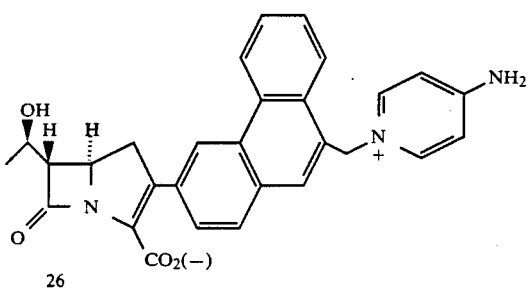

IR (KBr): 1755 (β-lactam), 1655 (iminium), 1590 cm⁻¹ (carboxylate).

UV (H₂O): λmax=330 nm (ε=18,400)

EXAMPLE 25

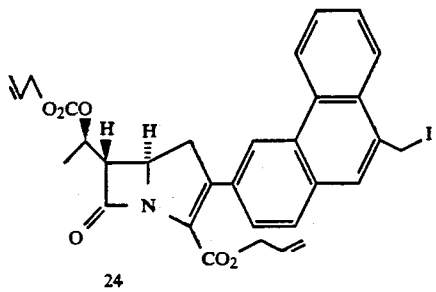

Allyl-(5R,6S)-2-[9-(2-aminopyridinium)methyl-3-phenanthrenyl]-6-[1R-(allyloxycarbonyloxy)ethyl]-carbapen-2-em-3-carboxylate chloride (27) and Allyl-(5R,6S)-2-{9-[(2-pyridyl)amino]methyl-3-phenanthrenyl}-6-[1R-(allyloxycarbonyloxy)ethyl]-carbapen-2-em-3-carboxylate (28)

To a solution of the iodide 24 (108.5 mg, 0.170 mmol) in 1.5 ml of acetonitrile was added dropwise a solution of 2-aminopyridine in acetonitrile (0.57M, 0.37 ml). The reaction mixture was stirred at room temperature for 2 hours and then at 0° C. for 12 hours at which point TLC analysis indicated that a considerable amount of unreacted 24 remained. Silver trifluoromethanesulfonate (46 mg, 0.18 mmol) was added, which resulted in rapid reaction of the remaining iodide. The reaction mixture was filtered through Celite, washing with methylene chloride. The filtrate was diluted with methylene chloride and washed with water and brine. Drying (Na₂SO₄) and evaporation gave a yellow semi-solid which consisted of two components which were separated as follows. The crude product mixture was dissloved in a small volume of methylene chloride in a centriguge

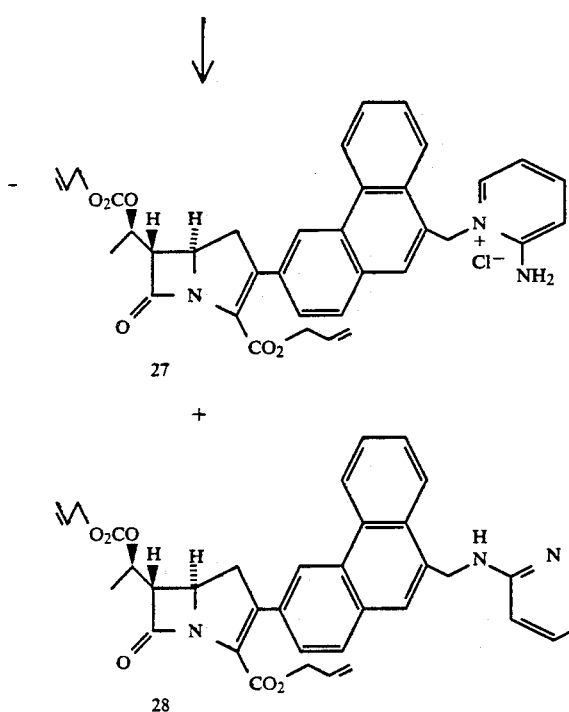

tube and the less soluble product 27 was precipitated by the addition of ethyl ether. The solid was isolated by centrifugation, washing once with ethyl ether, and after drying in vacuo 51.5 mg (40%) of carbapenem 27 was obtained as a yellow solid. The supernatant solution which had been removed from the above solid was evaporated to provide 29 mg (27%) of carbapenem 28 as a yellow oil.

27

¹H-NMR(300 MHz, CDCl₃): δ 1.50 (d, J=6.04 Hz, 3H, CH₃), 3.25–3.60 (m, 3H, H1, H6), 4.36 (broad t, J=9 Hz, 1H, H5), 4.45–4.75 (m, 4H, —OCH₂C=C), 5.0–5.5 (m, 5H, H8, —CH=CH₂), 5.66 (bs, 2H, —CH₂N), 5.6–6.0 (m, 2H, —CH=C), 6.3–6.5 (m, 1H), 7.05 (d, J=5.6 Hz, 1H), 7.3–7.9 (m, 8H), 8.5–9.0 (m, 4H).

28

¹H-NMR(300 MHz, CDCl₃): δ 1.52 (d, J=6.41 Hz, 3H CH₃), 3.30–3.55 (m, 3H, H1, H6), 4.36 (ddd, J=2.7, 8.9, 9.8 Hz, 1H, H5), 4.55–4.80 (m, 4H, —OCH₂C=C), 4.99 (d, J=4.9 Hz, 2H, —CH₂N), 5.05–5.45 (m, 5H, H8, —C=CH₂), 5.75–6.05 (m, 2H, —CH=C), 6.42 (d, J=7.8 Hz, 1H), 6.63 (dd, J=5.5, 7.1 Hz 1H), 7.35–7.85 (m, 6H), 8.05–8.20 (m, 2H), 8.60–8.75 (m, 2H).

EXAMPLE 26

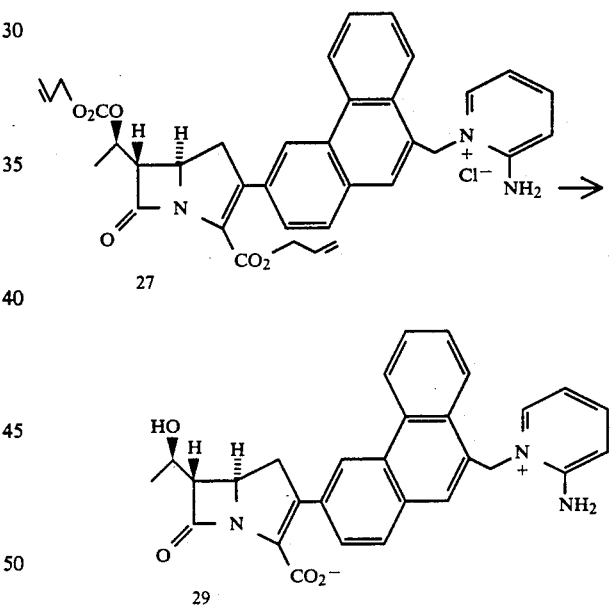

(5R,6S)-2-[9-(2-aminopyridinium)methyl-3-phenanthrenyl]-6-(1R-hydroxyethyl)-carbapen-2-em-3-carboxylate (29)

In an analogous manner to that described in Example 24, 51.5 mg (0.0704 mmol) of carbapenem 27 was deprotected to yield 5.7 mg (17%) of the title compound as a yellow solid.

¹H-NMR (300 MHz, 2:1 D₂O/CD₃CN): δ 1.66 (d, J=6.47 Hz, 3H, CH₃), 3.54 (dd, J=9.8, 16.6 Hz, 1H, H1a), 3.83 (dd, J=2.7, 6.0 Hz, 1H, H6), 3.92 (dd, J=8.5, 16.6 Hz, 1H, H1b), 4.54–4.72 (m, 2H, H5, H8), 6.11 (s, 2H, —CH₂N), 7.26 (t, J=7Hz, 1H), 7.6 (d, partially obscured, 1H), 7.62 (s, 1H), 7.96–8.36 (m, 7H), 9.04 (s, 1H), 9.17 (d, J=7.8 Hz, 1H).

IR(KBr): 1755 (β-lactam), 1670 (iminium), 1585 cm⁻¹ (carboxylate).
UV(H₂O): λmax=323 nm (ε=17,000).

EXAMPLE 27

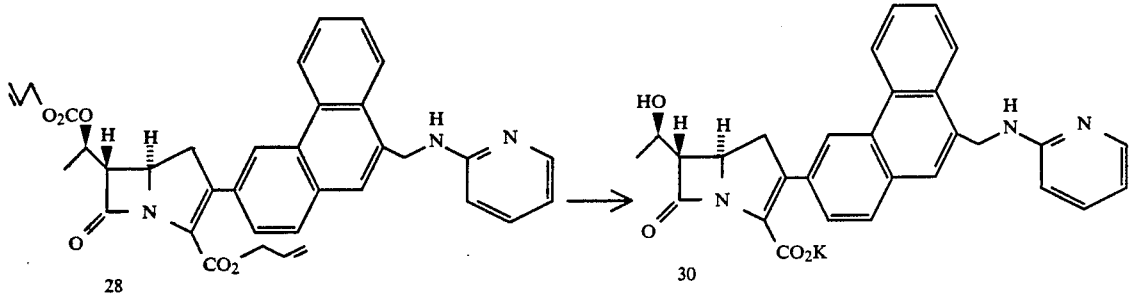

Potassium (5R,6S)-2-{9-[(2-pyridyl)amino]methyl-3-phenanthrenyl}-6-[1R-(allyloxycarbonyloxy)ethyl]carbapen-2-em-3-carboxylate (30)

In an analogous manner to that described in Example 24, 29 mg (0.048 mmol) of carbapenem 28 was de-allylated to yield 8.3 mg (33%) of the title compound as an off-white lyophilized solid.

¹H-NMR (300 MHz, 2:1 D₂O/CD₃CN): δ 1.63 (d J=6.35 Hz, 3H, CH₃), 3.53 (dd, J=9.8, 16.7 Hz, 1H, H1a), 3.80 (dd, J=2.7, 6.0 Hz, 1H, H6), 3.91 (dd, J=8.6, 16.7 Hz, 1H, H1b), 4.5–4.7(m, 2H, H5, H8), 5.26 (s, 2H, —CH₂N), 6.91 (d, J=8.2 Hz, 1H), 7.0 (t, J=6 Hz, 1H), 7.83 (dt, J=1.5, 8 Hz, 1H), 7.9–8.2 (m, 5H), 8.3 (bs, 1H), 8.47 (dd, J=1.5, 8 Hz, 1H), 9.02 (s, 1H), 9.12 (d, J=8.3 Hz, 1H).

IR (KBr): 1750 (β-lactam), 1605 cm⁻¹ (carboxylate).
UV (H₂O): λmax=324 nm (ε=21,400).

EXAMPLES 28–32

Operating as described in the previous examples, the following compounds were analogously prepared:

| Example No. | X | M | H₂O λmax |
|---|---|---|---|

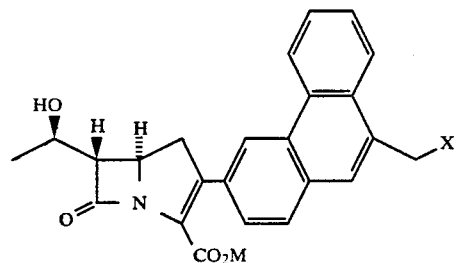

28    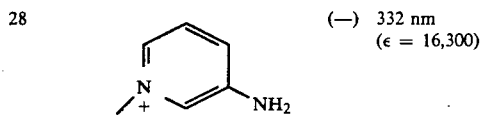    (—) 332 nm (ε = 16,300)

29    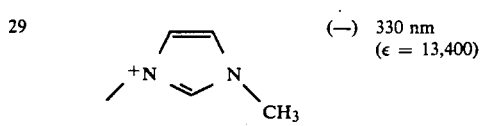    (—) 330 nm (ε = 13,400)

-continued

| Example No. | X | M | H₂O λmax |
|---|---|---|---|

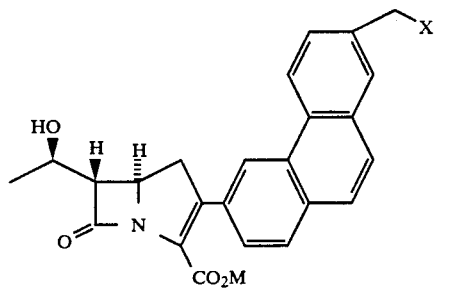

30    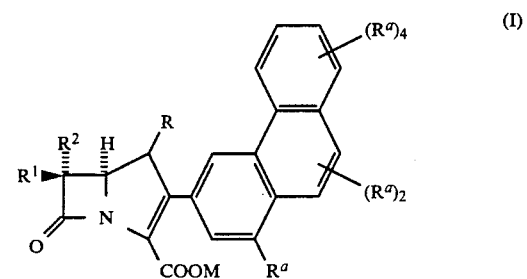

30 — NH₂ on pyridinium    (—) 327 nm (ε = 17,800)

31 — 2-amino-N-methylpyridinium    (—) 320 nm (ε = 18,400)

32 — N-methylimidazolium    (—) 325 nm (ε = 16,600)

What is claimed is:
1. A compound of the formula:

(I)

wherein:
R is H or CH₃;
R¹ and R² are independently H, CH₃—, CH₃CH₂—, (CH₃)₂CH—, HOCH₂—, CH₃CH(OH)—, (CH₃)₂C(OH)—, FCH₂CH(OH)—, $F_2CHCH(OH)$—, $F_3CCH(OH)$—, $CH_3CH(F)$—, $CH_3CF_2$—, or $(CH_3)_2C(F)$—;

$R^a$ are independently selected from the group consisting of hydrogen and the radicals set out below, provided that one but not more than one $R^a$ is selected from Type I substituents, the remaining non-hydrogen substituents being selected from Type II, and in total not more than four $R^a$ radicals are other than hydrogen:

I.

(a)

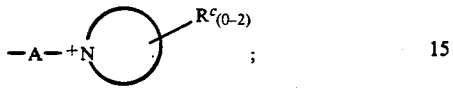

where

A is $(CH_2)_m$—Q—$(CH_2)_n$, where m is 0 to 6 and n is 1 to 6 and Q is a covalent bond, O, S, SO, $SO_2$, NH, —$SO_2NH$—, —$NHSO_2$—, —CONH—, —NHCO—, —$SO_2N(C_1$-$C_4$alkyl)—, —$N(C_{1-C4}$alkyl)$SO_2$—, —$CON(C_1$-$C_4$alkyl)—, —$N(C_{1-C4}$alkyl)CO—, —CH=CH—, —CO—, —OC(O)—, —C(O)O— or $N(C_{1-C4}$alkyl) and $(CH_2)_m$ is attached to the phenanthrenyl moiety;

is a 5- or 6-membered monocyclic heterocycle or an 8-, 9- or 10-membered bicylic heterocycle, the heterocycle containing a first nitrogen in an aromatic 5- or 6-membered first ring, with attachment of the heterocycle to A by way of said first nitrogen and said first nitrogen is quaternary by virtue of the attachment and ring bonds, with the first ring containing 0 or 1 of either O or S, with the first ring containing 0 to 3 additional nitrogen atoms, with the first ring optionally fused to a 3- or 4-membered moiety to form the optional second ring, with the the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is $R^a$ as defined under II below, hydrogen, or —$NR^YR^z$ (where $R^Y$ and $R^Z$ are defined in II below), but independently selected from $R^a$ and from each other if more than one $R^c$ is present, and is attached to a carbon ring atom or a nitrogen heteroatom the valency of which is not satisfied by the ring bonds;

(b)

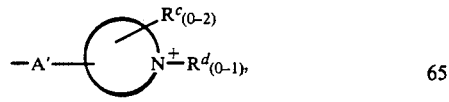

where

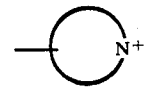

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen quaternary by virtue of a substituent $R^d$ in addition to the ring bonds thereto, with said first nitrogen neutral in the absence of a substituent Rd, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is defined above;

$R^d$ is hydrogen, $NH_2$, $O^-$ or $C_1$-$C_4$alkyl (where the alkyl group is optionally mono-substituted with $R^q$ as defined under IIc below);

A' is $(CH_2)_m$—Q—$(CH_2)_n$, where m is 0 to 6 and n is 0 to 6, Q is given above, and when m and n are 0 then Q is not a covalent bond;

(c) —$A_p$—$N^+R^y(R^w)_{(0-1)}(R^z)$ where $R^y$ and $R^z$ are as defined under II below, $R^y$ and $R^z$ may further be together a $C_2$-$C_4$ alkylidene radical to form a ring (optionally mono-substituted with $R^q$ as defined below) interrupted by $N(O)R^e$ or $N^+(R^e)_2$ (where $R^e$ is hydrogen, $C_1$-$C_4$alkyl, or $C_1$-$C_4$alkyl substituted with $R^q$ defined below), $R^w$ is hydrogen, $C_{1-4}$alkyl, $O^-$, $NH_2$ or absent in which case the $N^+$ is neutral, $R^w$, $R^y$ and $R^z$ may further together form a $C_5$-$C_{10}$ tertiary alkylidene radical which with $N^+$ forms a bicyclic ring, where the tertiary alkylidene radical is optionally mono-substituted with $R^q$ as defined below and where the tertiary carbon of the tertiary alkylidene radical is optionally replaced with nitrogen, $N^+R^e$ (where $R^e$ is defined above), or $N^+$—$O^-$, p is 0 or 1, and A is as defined above;

(d)

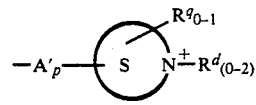

where

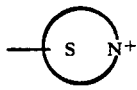

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen quaternary by virtue of one or two substituents $R^d$ in addition to the ring bonds thereto, with the first nitrogen alternatively neutral by virtue of zero or one substituents $R^d$ in addition to the ring bonds thereto, with attachment of the heterocycle to $A'$ by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), S(O)$_2$ and NR$^e$ where R$^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

$R^d$ is defined above and where more than one $R^d$ is present on a nitrogen, at least one $R^d$ is hydrogen or $C_1$–$C_4$alkyl;

$A'$ is defined above; and p is defined above;

$R^q$ is defined below;

II.
(a) a trifluoromethyl group: —CF$_3$;
(b) a halogen atom: —Br, —Cl, —F, or —I;
(c) $C_1$–$C_4$ alkoxy radical: —OC$_{1-4}$ alkyl, wherein the alkyl is optionally mono-substituted by R$^q$, where
 R$^q$ is a member selected from the group consisting of —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen or an alkali metal);
(d) a hydroxy group: —OH;
(e) a carbonyloxy radical: —O(C=O)R$^s$, where R$^s$ is $C_{1-4}$ alkyl or phenyl, each of which is optionally mono-substituted by R$^q$ as defined above;
(f) a carbamoyloxy radical: —O(C=O)N(R$^y$)R$^z$ where
 R$^y$ and R$^z$ are independently H, $C_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)— or —S(O)$_2$—, to form a ring (where the ring is optionally mono-substituted with R$^q$ as defined above);
(g) a sulfur radical: —S(O)$_n$—R$^s$ where n=0–2, and R$^s$ is defined above;
(h) a sulfamoyl group: —SO$_2$N(R$^y$)R$^z$ where R$^y$ and R$^z$ are as defined above;
(i) azido: N$_3$
(j) a formamido group: —N(R$^t$)(C=O)H, where R$^t$ is H or $C_{1-4}$ alkyl, and the alkyl thereof is optionally mono-substituted by R$^q$ as defined above;
(k) a ($C_1$–$C_4$ alkyl)carbonylamino radical: —N(R$^t$)(C=O)C$_{1-4}$ alkyl, where R$^t$ is as defined above, and the alkyl group is also optionally mono-substituted by R$^q$ as defined above;
(l) a ($C_1$–$C_4$ alkoxy) carbonylamino radical: —N(R$^t$)(C=O)OC$_{1-4}$ alkyl, where R$^t$ is as defined above, and the alkyl group is also optionally mono-substituted by R$^q$ as defined above;
(m) a ureido group: —N(R$^t$)(C=O)N(R$^y$)R$^z$ where R$^t$, R$^y$ and R$^z$ are as defined above;
(n) a sulfonamido group: —N(R$^t$)SO$_2$R$^s$, where R$^s$ and R$^t$ are as defined above;
(o) a cyano group: —CN;
(p) a formyl or acetalized formyl radical: —(C=O)H or —CH(OCH$_3$)$_2$;
(q) ($C_1$–$C_4$ alkyl)carbonyl radical wherein the carbonyl is acetalized: —C(OCH$_3$)$_2$C$_{1-4}$ alkyl, where the alkyl is optionally mono-substituted by R$^q$ as defined above;
(r) carbonyl radical: —(C=O)R$^s$, where R$^s$ is as defined above;
(s) a hydroximinomethyl radical in which the oxygen or carbon atom is optionally substituted by a $C_1$–$C_4$ alkyl group: —(C=NOR$^z$)R$^y$ where R$^y$ and R$^z$ are as defined above, except they may not be joined together to form a ring;
(t) a ($C_1$–$C_4$ alkoxy)carbonyl radical: —(C=O)OC$_{1-4}$ alkyl, where the alkyl is optionally mono-substituted by R$^q$ as defined above;
(u) a carbamoyl radical: —(C=O)N(R$^y$)R$^z$ where R$^y$ and R$^z$ are as defined above;
(v) an N-hydroxycarbamoyl or N($C_1$–$C_4$ alkoxy)carbamoyl radical in which the nitrogen atom may be additionally substituted by a $C_1$–$C_4$ alkyl group: —(C=O)—N(OR$^y$)R$^z$ where R$^y$ and R$^z$ are as defined above, except they may not be joined together to form a ring;
(w) a thiocarbamoyl group: —(C=S)N(R$^y$)(R$^z$) where R$^y$ and R$^z$ are as defined above;
(x) carboxyl: —COOM$^b$, where M$^b$ is as defined above;
(y) thiocyanate: —SCN;
(z) trifluoromethylthio: —SCF$_3$;
(aa) tetrazolyl, where the point of attachment is the carbon atom of the tetrazole ring and one of the nitrogen atoms is mono-substituted by hydrogen, an alkali metal or a $C_1$–$C_4$ alkyl optionally substituted by R$^q$ as defined above;
(ab) an anionic function selected from the group consisting of: phosphono [P=O(OM$^b$)$_2$]; alkylphosphono {P=O(OM$^b$)-[O($C_1$–$C_4$ alkyl)]}; alkylphosphinyl [P=O(OM$^b$)-($C_1$–$C_4$alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$MN-$^b$CON(R$^y$)R$^z$; and SO$_2$NM$^b$CN, where R$^x$ is phenyl or heteroaryl, where heteroaryl is a monocylclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

(ac) C$_5$-C$_7$ cycloalkyl group in which one of the carbon atoms in the ring is replaced by a heteroatom selected from O, S, NH or N(C$_1$-C$_4$ alkyl) and in which one additional carbon atom may be replaced by NH or N(C$_1$-C$_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

(ad) C$_2$-C$_4$ alkenyl radical, optionally mono-substituted by one of the substituents (a) to (ac) above and phenyl which is optionally substituted by R$^q$ as defined above;

(ae) C$_2$-C$_4$ alkynyl radical, optionally mono-substituted by one of the substituents (a) to (ac) above;

(af) C$_1$-C$_4$ alkyl radical;

(ag) C$_1$-C$_4$ alkyl mono-substituted by one of the substituents (a)-(ac) above;

(ah) a 2-oxazolidinonyl moiety in which the point of attachment is the nitrogen atom of the oxazolidinone ring, the ring oxygen atom is optionally replaced by a heteroatom selected from —S— and NR$^t$ (where R$^t$ is as defined above) and one of the saturated carbon atoms of the oxazolidinone ring is optionally mono-substituted by one of the substituents (a) to (ag) above;

M is selected from:
(i) hydrogen;
(ii) a pharmaceutically acceptable esterifying group or removable carboxyl protecting group;
(iii) an alkali metal or other pharmaceutically acceptable cation; or
(iv) a negative charge which is balanced by a positively charged group.

2. A compound according to claim 1 wherein R$^1$ is hydrogen and R$^2$ is (R)—CH$_3$CH(OH)— or (R)—CH$_3$CH(F)—.

3. The compound of claim 2 wherein said Type I.a. substituents are selected from the group consisting of:

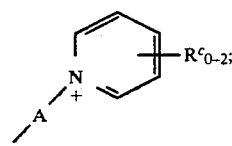

-continued

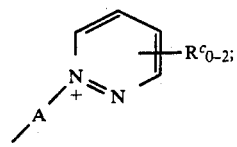

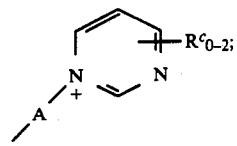

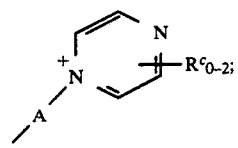

where the ring contains three carbon atoms;

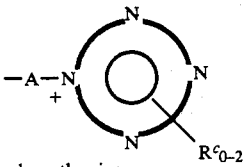

where the ring contains two carbon atoms;

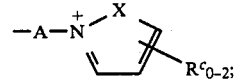

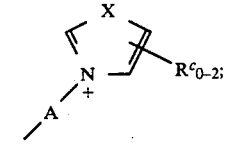

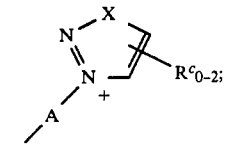

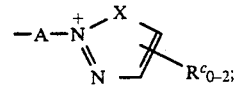

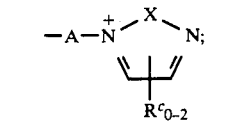

-continued
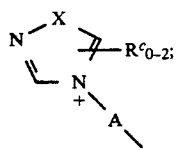
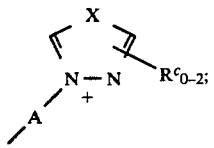
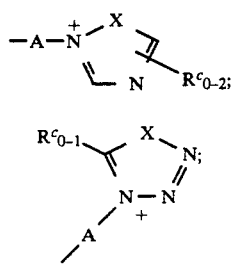
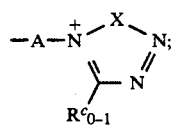
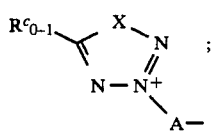
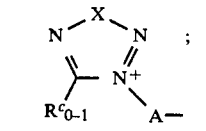
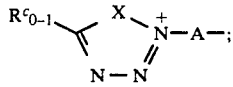
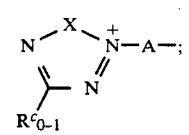
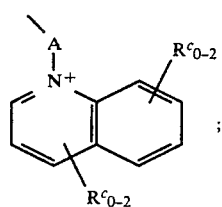
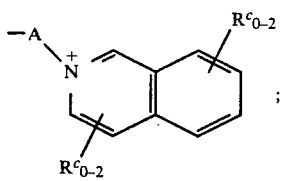
-continued
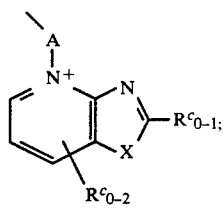
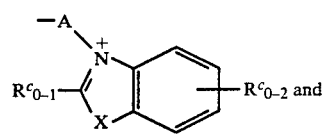
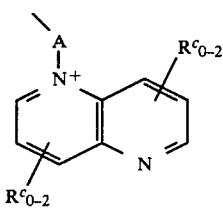
where X=O, S, or $NR^c$.
4. The compound of claim 2 wherein said Type I.b. substituents are selected from the group consisting of:
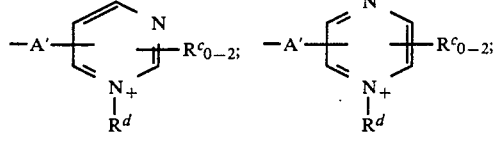
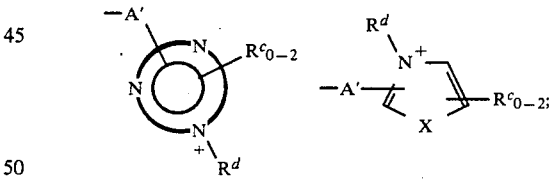
where the ring contains three carbon atoms;
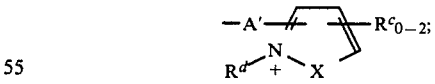
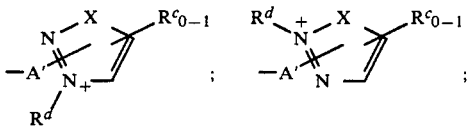
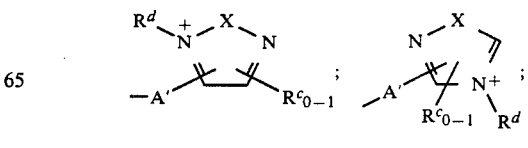

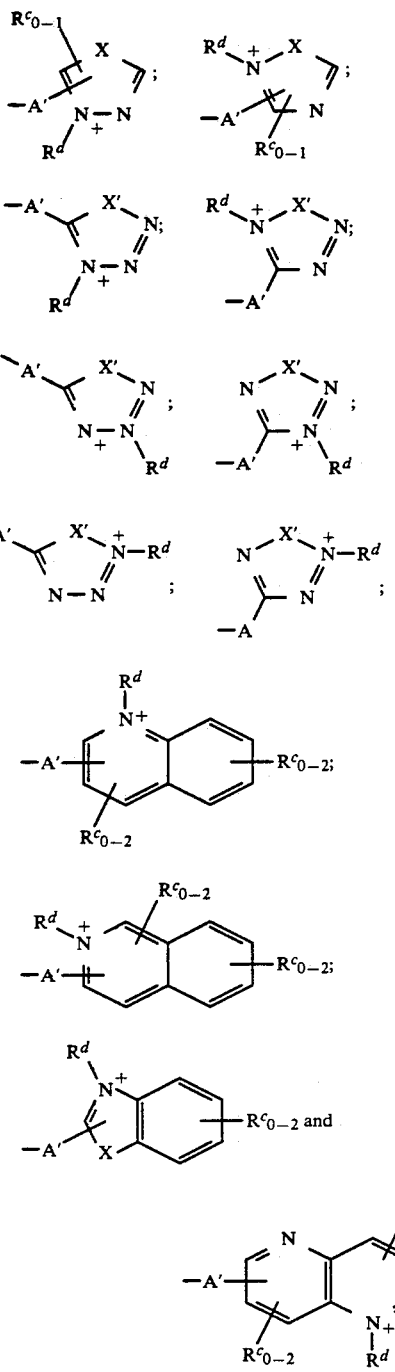

where X=O, S, or NR$^c$ and X'=O or S.

5. The compound of claim 2 wherein said Type I.c. substituents are selected from the group consisting of:

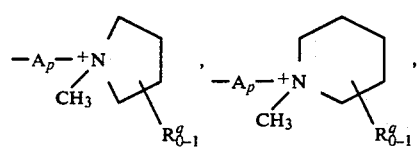

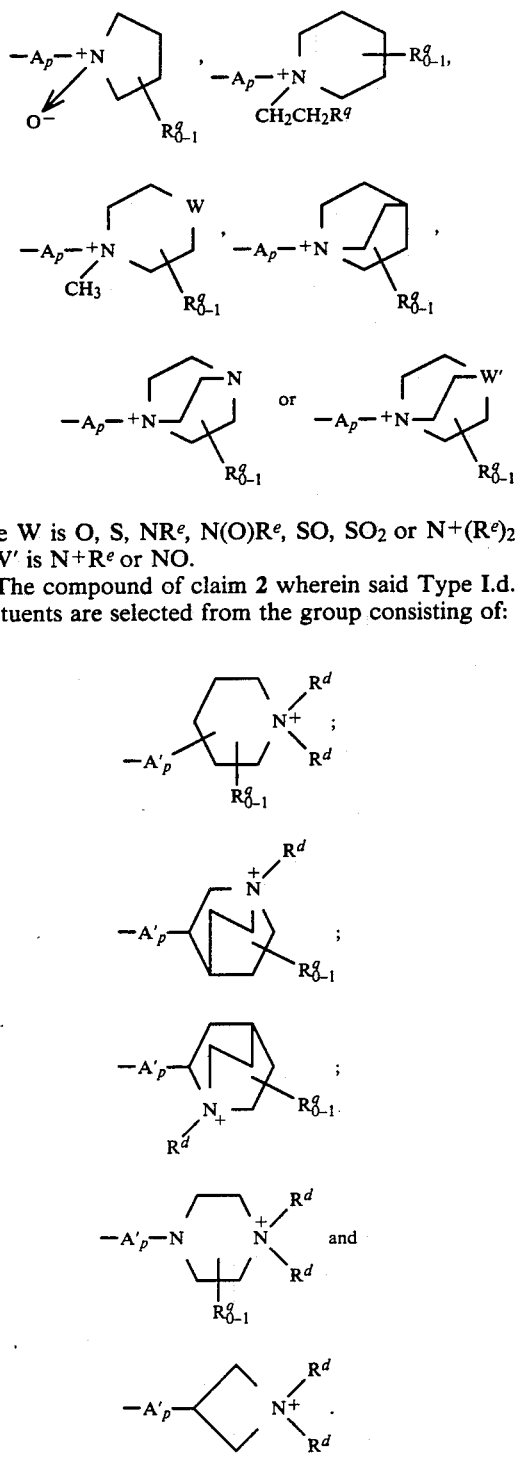

where W is O, S, NR$^e$, N(O)R$^e$, SO, SO$_2$ or N+(R$^e$)$_2$ and W' is N+R$^e$ or NO.

6. The compound of claim 2 wherein said Type I.d. substituents are selected from the group consisting of:

7. The compound of claim 2 wherein said R$^c$ where attached to a ring carbon atom is selected from the group consisting of —NH$_2$, —SCH$_3$, —SOCH$_3$, —CH$_2$OH, —(CH$_2$)$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, CH$_2$CH$_3$, CH$_2$CONH$_2$ and CH$_2$CON(C$_1$-C$_4$alkyl) where M$^b$ is defined above.

8. The compound of claim 2 wherein said R$^c$ where attached to a neutral ring nitrogen atom is selected from the group consisting to —CH₂OH, —(CH₂)₂OH, —CH₂COOM$^b$, —CH₂CH₂COOM$^b$, —CH₂SOCH₃, —CH₂SCH₃, —CH₂SO₃M$^b$, —CH₂CH₂SO₃M$^b$, —CH₃, CH₂CH₃, CH₂CONH₂ and CH₂CON(C₁-C₄alkyl) where M$^b$ is defined above.

9. The compound of claim 2 wherein R$^d$ is selected from the group consisting of hydrogen, —CH₃, CH₂CH₃, —CH₂CH₂CH₃, —CH₂COOM$^b$, —CH₂SO₃M$^b$, —NH₂ and O$^{(-)}$, where M$^b$ is defined above.

10. The compound of claim 2 wherein A is selected from the group consisting of —CH₂—, —CH₂CH₂—, —CH₂CH₂CH₂—, —CH₂CH₂CH₂CH₂—, —OCH₂CH₂—, —SOCH₂—, —SO₂CH₂—, —SCH₂CH₂—, —SOCH₂CH₂—, —SO₂CH₂CH₂—, —NHCH₂CH₂—, —N(CH₃)CH₂CH₂—, —CH₂N(CH₃)CH₂CH₂—, —CONHCH₂CH₂—, —SO₂NHCH₂CH₂—, —COCH₂—, —CH=CHCH₂— and —CH₂OCH₂CH₂—.

11. The compound of claim 2 wherein A' is selected from the group consisting of —CH₂—, —CH₂CH₂—, —CH₂CH₂CH₂—, —CH₂CH₂CH₂CH₂—, —OCH₂CH₂—, —SOCH₂—, —SO₂CH₂—, —SCH₂CH₂—, —SOCH₂CH₂—, —SO₂CH₂CH₂—, —NHCH₂CH₂—, —N(CH₃)CH₂CH₂—, —CH₂N(CH₃)CH₂CH₂—, —CONHCH₂CH₂—, —SO₂NHCH₂CH₂—, —COCH₂—, —CH=CHCH₂—, —CH₂OCH₂CH₂—, —O—, —S—, —NH—, —SO₂—, —SO₂NH—, —CONH—, —CH=CH—, —CH₂S—, —CH₂NH—, —CONHCH₂— and —SO₂NHCH₂—.

12. The compound of claim 2 wherein said Type II substitutents are selected from the group consisting of:

| | |
|---|---|
| —OCH₃ | —OCH₂CO₂Na |
| —OCH₂CH₂OH | —CF₃ |
| —F | —Cl |
| —Br | —I |
| —OH | —OCOCH₃ |
| —OCONH₂ | —SCH₃ |
| —SOCH₃ | —SO₂CH₃ |
| —SCH₂CH₂OH | —SOCH₂CH₂OH |
| —SO₂NH₂ | —SO₂N(CH₃)₂ |
| —NHCHO | —NHCOCH₃ |
| —NHCO₂CH₃ | —NHSO₂CH₃ |
| —CN | —CHO |
| —COCH₃ | —COCH₂OH |
| —CH=NOH | —CH=NOCH₃ |
| —CH=NOCH₂CO₂H | —CH=NOCMe₂CO₂H |
| —CH=NOCMe₂CO₂Me | —CO₂CH₂CH₂OH |
| —CONH₂ | —CONHCH₃ |
| —CON(CH₃)₂ | —CONHCH₂CN |
| —CONHCH₂CONH₂ | —CONHCH₂CO₂H |
| —CONHOH | —CONHOCH₃ |
| —tetrazolyl | —CO₂Na |
| —SCF₃ | —PO₃NaH |
| —CONHSO₂Ph | —CONHSO₂NH₂ |
| —SO₃Na | —SO₂NHCN |
| —SO₂NHCONH₂ | —CH=CHCN |
| —CH=CHCONH₂ | —CH=CHCO₂Na |
| —C≡C—CONH₂ | —C≡C—CN |
| —CH₂OH | —CH₂N₃ |
| —CH₂CO₂Na | SO₂CH₂C₂OH and —CH₂I. |

13. The compounds of claim 2 having the formula:

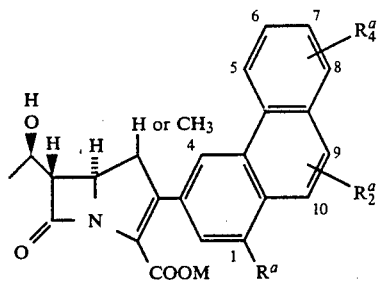

wherein M and R$^a$ are selected from the group consisting of:

| M | R$^a$ | R$^a$ Position |
|---|---|---|
| (−) | —CH₂N⁺(pyridyl)NH₂ | 1 |
| (−) | —CH₂N⁺(pyridyl)NH₂ | 7 |
| (−) | —CH₂N⁺(pyridyl)NH₂ | 8 |
| (−) | —CH₂N⁺(pyridyl)NH₂ | 9 |
| (−) | —CH₂N⁺(pyridyl)NH₂ | 10 |
| (−) | —CH₂N⁺(pyridyl)-NH₂ | 1 |
| (−) | —CH₂N⁺(pyridyl)-NH₂ | 7 |
| (−) | —CH₂N⁺(pyridyl)-NH₂ | 8 |
| (−) | —CH₂N⁺(pyridyl)-NH₂ | 9 |

| | | |
|---|---|---|
| (−) | 4-aminopyridinium-CH₂ | 10 |
| (−) | −CH₂N⁺(imidazole)N−CH₃ | 1 |
| (−) | −CH₂N⁺(imidazole)N−CH₃ | 7 |
| (−) | −CH₂N⁺(imidazole)N−CH₃ | 8 |
| (−) | −CH₂N⁺(imidazole)N−CH₃ | 9 |
| (−) | −CH₂N⁺(imidazole)N−CH₃ | 10 |
| (−) | −CH₂N⁺(pyrazole)N−CH₃ | 9 |
| (−) | −CH₂N⁺(pyrazole)N−CH₃ | 9 |
| (−) | −CH₂N⁺(imidazole)NCH₂CONH₂ | 9 |
| (−) | −CH₂N⁺(pyrazoline)-N−CH₃ | 9 |
| (−) | −CH₂N⁺(imidazole)N−CH₂SOCH₃ | 9 |
| K | −CH₂N⁺(imidazole)NCH₂SO₃⁻ | 9 |
| K | −CH₂N⁺(imidazole)NCH₂CO₂⁻ | 9 |
| K | 4-(CH₂CH₂SO₃⁻)-pyridinium-CH₂ | 9 |
| K | 3-(CO₂⁻)-pyridinium-CH₂ | 9 |
| (−) | −CH₂N⁺(imidazole)NCH₂CH₂OH | 7 |
| (−) | 3-amino-pyridinium-CH₂ | 9 |
| (−) | 2-amino-4-(CH₂SCH₃=O)-pyridinium-CH₂ | 9 |
| (−) | 4-(CH₂OH)-pyridinium-CH₂ | 9 |
| (−) | 3-amino-5-(CH₂OH)-pyridinium-CH₂ | 9 |
| (−) | −CH₂N⁺H(CH₃)₂ | 9 |
| (−) | −CO₂CH₂CH₂N⁺H(CH₃)₂ | 1 |
| (−) | −NSO₂CH₂CH₂N⁺(imidazole)N−CH₃, H | 1 |
| (−) | −OCH₂CH₂N⁺(2-aminopyridinium) | 9 |
| (−) | −SCH₂CH₂N⁺(2-aminopyridinium) | 1 |
| (−) | −SO₂CH₂CH₂N⁺(2-aminopyridinium) | 9 |
| (−) | −CH₂OCH₂CH₂N⁺(2-aminopyridinium) | 1 |

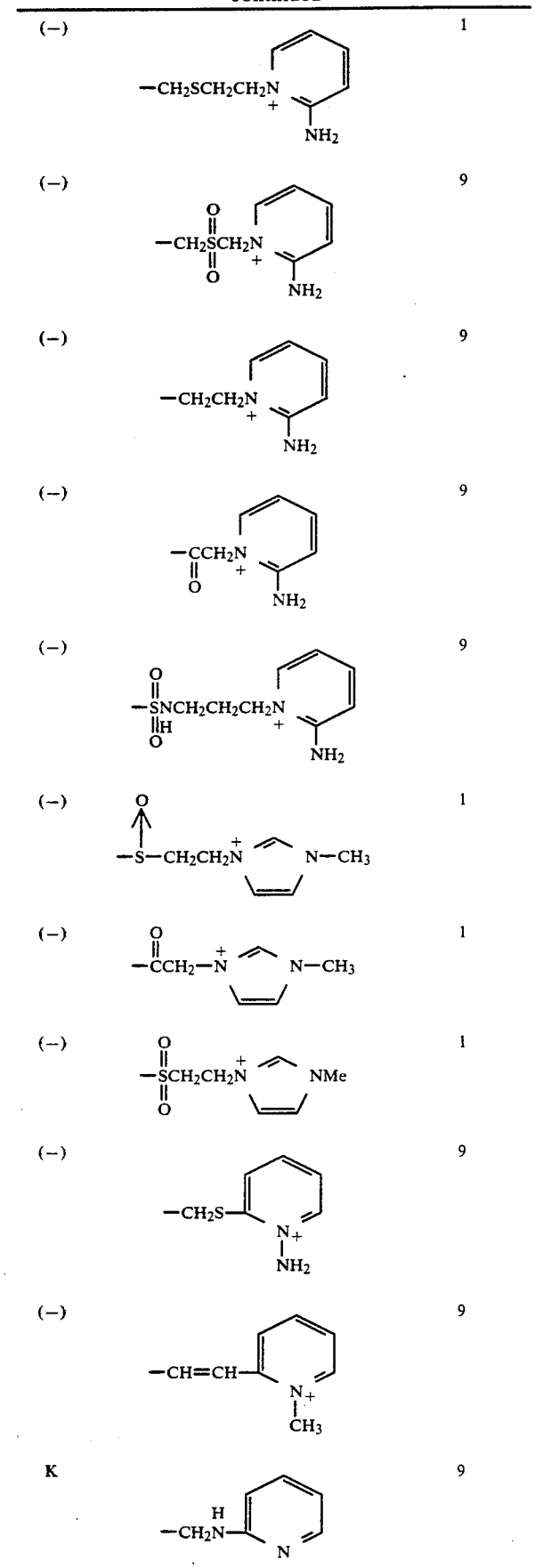
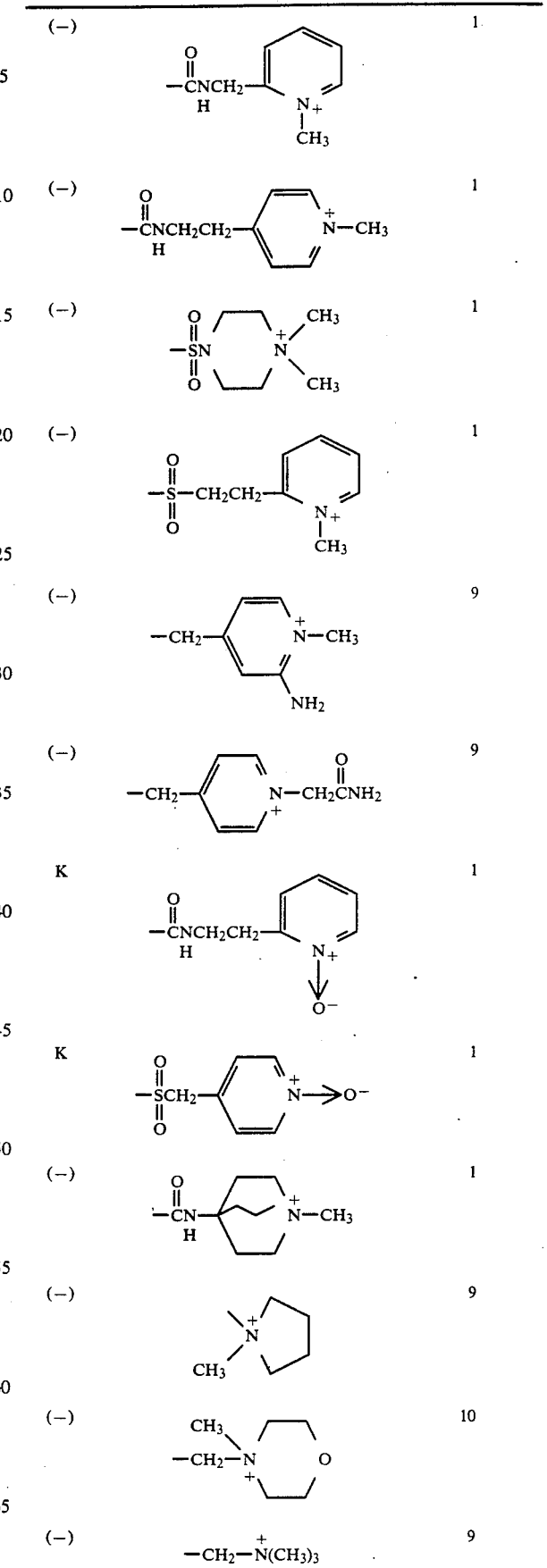

-continued

| M | $R^a$ | $R^a$ Position | $R^{a'}$ | $R^{a'}$ Position |
|---|---|---|---|---|
| (−) | [piperidinylmethyl cation] | | | 9 |
| K | [carboxylate-piperidinylmethyl] | | | 9 |
| K | [N-oxide morpholinylmethyl] | | | 7 |
| (−) | [piperazine N-oxide methyl] | | | 10 |
| (−) | −C(O)NH−CH$_2$− [N,N-dimethylpiperidinium] | | | 1 |
| (−) | CN | 1 | −CH$_2$N$^+$(imidazolium NCH$_3$) | 9 |
| (−) | SOCH$_3$ | 1 | −CH$_2$N$^+$(imidazolium NCH$_3$) | 9 |
| (−) | CO$_2$K | 1 | −CH$_2$N$^+$(imidazolium NCH$_3$) | 9 |
| (−) | CO$_2$K | 1 | −CH$_2$N$^+$-aniline (NH$_2$) | 9 |
| (−) | [tetrazole NK] | 1 | −CH$_2$N$^+$-aniline (NH$_2$) | 7 |
| (−) | [tetrazole NK] | 1 | −CH$_2$N$^+$-aniline (NH$_2$) | 9 |
| (−) | SO$_3$K | 1 | −CH$_2$N$^+$-aniline (NH$_2$) | 9 |
| (−) | CO$_2$K | 1 | N$^+$(CH$_3$)-pyrrolidinium | 10 |
| (−) | SO$_3$K | 1 | −CH$_2$−N$^+$(CH$_3$)-pyrrolidinium | 7 |
| (−) | SO$_3$K | 7 | −CH$_2$−N$^+$(CH$_3$)-pyrrolidinium | 9 |
| (−) | CHO | 1 | −CH$_2$N$^+$-(2-aminopyridinium) | 9 |

14. A compound according to claim 2 wherein there is at least one $R^a$ other than hydrogen in the 1-, 9-, or 10-position.

15. A compound according to claim 2 wherein there is, in total, up to two $R^a$ substituents other than hydrogen in the 1-, 9- or 10-position.

16. A composition comprising a pharmaceutically acceptable carrier and from 0.1% to about 99% by weight of active material of claim 1.

17. A composition according to claim 16 which further comprises an inhibitorily effective amount of a DHP inhibitor.

18. A composition according to claim 17 wherein said DHP inhibitor is 7-(L-2-amino-2-carboxyethylthio)-2-(2,2-dimethylcyclopropanecarboxamide)-2-heptanoic acid.

19. A method for treating bacterial infection in mammals comprising administering an effective amount of a compound of claim 1 and a pharmaceutically acceptable carrier therefor.

20. A method according to claim 19 which further comprises administering an inhibitorily effective amount of a DHP inhibitor.

21. A method according to claim 20 wherein said DHP inhibitor is 7-(L-2-amino-2-carboxyethylthio)-2-(2,2-dimethylcyclopropanecarboxamide)-2-heptanoic acid.

* * * * *